(12) United States Patent
Izatt et al.

(10) Patent No.: US 9,279,659 B2
(45) Date of Patent: Mar. 8, 2016

(54) SYSTEMS AND METHODS FOR COMPLEX CONJUGATE ARTIFACT RESOLVED OPTICAL COHERENCE TOMOGRAPHY

(75) Inventors: Joseph A. Izatt, Raleigh, NC (US); Al-Hafeez Dhalla, Durham, NC (US)

(73) Assignee: Duke University, Durham, NC (US)

( * ) Notice: Subject to any disclaimer, the term of this patent is extended or adjusted under 35 U.S.C. 154(b) by 561 days.

(21) Appl. No.: 13/355,381

(22) Filed: Jan. 20, 2012

(65) Prior Publication Data

US 2012/0188555 A1 Jul. 26, 2012

Related U.S. Application Data

(60) Provisional application No. 61/434,859, filed on Jan. 21, 2011.

(51) Int. Cl.
*G01B 9/02* (2006.01)
*A61B 3/10* (2006.01)

(52) U.S. Cl.
CPC ............ *G01B 9/02091* (2013.01); *A61B 3/102* (2013.01); *G01B 9/0201* (2013.01); *G01B 9/02004* (2013.01); *G01B 9/02078* (2013.01)

(58) Field of Classification Search
CPC ............... A61B 3/102; G01B 9/02004; G01B 9/02078; G01B 9/02091; G01B 9/0201; G01B 9/02
USPC .................................................. 356/479, 497
See application file for complete search history.

(56) References Cited

U.S. PATENT DOCUMENTS

| | | |
|---|---|---|
| 4,052,889 A | 10/1977 | Mucciardi et al. |
| 5,491,524 A | 2/1996 | Hellmuth et al. |
| 5,588,435 A | 12/1996 | Weng et al. |
| 5,994,690 A | 11/1999 | Kulkarni et al. |
| 6,552,806 B1 * | 4/2003 | Swinford et al. ............. 356/512 |
| 6,618,152 B2 | 9/2003 | Toida |

(Continued)

FOREIGN PATENT DOCUMENTS

| | | |
|---|---|---|
| EP | 2427723 | 3/2012 |
| WO | WO 2010-129544 | 11/2010 |

OTHER PUBLICATIONS

Zhang et al, Removal of a mirror image and enchancement of the signal-to-noise ratio in Fourier-domain optical coherence tomgoraphy using an electro-optic phase modulator, Jan. 15, 2005, Optics Letters, vol. 30, No. 2, 147-149.*

(Continued)

*Primary Examiner* — Michael P Lapage
(74) *Attorney, Agent, or Firm* — Jenkins, Wilson, Taylor & Hunt, P.A.

(57) ABSTRACT

Systems and methods are disclosed for optical coherence tomography (OCT). For example, imaging can use optical phase modulators based on optical delay lines that, in conjunction with a swept-source laser, can be used to achieve heterodyne swept source optical coherence tomography (SSOCT). These techniques resolve the complex conjugate ambiguity in SSOCT, thereby doubling the usable imaging range. This increased imaging range has numerous important clinical applications in ophthalmology, cardiology and radiology, as well as applications in small animal and non-biological imaging. These methods are superior to prior disclosed methods requiring acousto-optic or electro-optic modulators with respect to complexity, efficiency, imaging speed and image quality.

18 Claims, 18 Drawing Sheets

(56) References Cited

U.S. PATENT DOCUMENTS

| | | | |
|---|---|---|---|
| 6,887,231 | B2 | 5/2005 | Mrochen et al. |
| 6,940,557 | B2 | 9/2005 | Handjojo et al. |
| 7,092,748 | B2 | 8/2006 | Valdes Sosa et al. |
| 7,102,756 | B2 | 9/2006 | Izatt et al. |
| 7,187,800 | B2 | 3/2007 | Hibbard |
| 7,330,270 | B2 | 2/2008 | O'Hara et al. |
| 7,486,406 | B2 | 2/2009 | Kim |
| 7,602,500 | B2 | 10/2009 | Izatt |
| 7,648,242 | B2 | 1/2010 | Ferguson et al. |
| 7,719,692 | B2 | 5/2010 | Izatt |
| 7,796,243 | B2 | 9/2010 | Choo-Smith et al. |
| 7,907,765 | B2 | 3/2011 | Fauver et al. |
| 7,990,541 | B2 | 8/2011 | Izatt |
| 8,149,418 | B2 | 4/2012 | Tearney et al. |
| 8,155,420 | B2 | 4/2012 | Meyer et al. |
| 8,565,499 | B2 | 10/2013 | Zhao et al. |
| 8,693,745 | B2 | 4/2014 | Izatt |
| 8,718,743 | B2 | 5/2014 | Izatt |
| 2005/0057756 | A1 | 3/2005 | Fang-Yen et al. |
| 2005/0171438 | A1 | 8/2005 | Chen et al. |
| 2007/0258094 | A1 | 11/2007 | Izatt et al. |
| 2008/0309881 | A1 | 12/2008 | Huang et al. |
| 2009/0185166 | A1 | 7/2009 | Oldenburg et al. |
| 2009/0257636 | A1 | 10/2009 | Wei et al. |
| 2009/0270738 | A1 | 10/2009 | Izatt |
| 2009/0290167 | A1* | 11/2009 | Flanders et al. ............... 356/497 |
| 2010/0124158 | A1* | 5/2010 | Leto ......................... 369/112.23 |
| 2010/0150467 | A1 | 6/2010 | Zhao |
| 2010/0309477 | A1* | 12/2010 | Yun et al. ....................... 356/497 |
| 2010/0309480 | A1* | 12/2010 | Furusawa et al. ............. 356/519 |
| 2011/0007321 | A1 | 1/2011 | Everett et al. |
| 2011/0032533 | A1 | 2/2011 | Izatt |
| 2014/0241605 | A1 | 8/2014 | Izatt |

OTHER PUBLICATIONS

Davis, A. M. et al., "Heterodyne swept-source optical coherence tomography for complete complex conjugate ambiguity removal," *Journal of Biomedial Optics*, vol. 10, No. 6, Nov./Dec. 2005.

Wieserlabs UG Data Sheet—1 GHz Dual-Balanced InGaAs Low Noise Photodetector No. WL-BPD1GA, www.wieserlabs.com Oct. 2011.

Yun, S. et al., "Removing the depth-degeneracy in optical frequency domain imaging with frequency shifting," *Optics Express*, vol. 12, No. 20, Oct. 4, 2004.

O. W. Richards, "Phase Difference Microscopy," Nature, 1944, vol. 154, No. 672.

C. R. Tilford, "Analytical procedure for determining lengths from fractional fringes," Appl. Opt. 16, 1977, pp. 1857-1860.

Y. Cheng and J. C. Wyant, "Two-wavelength phase shifting interferometry," Appl. Opt. 23, 1984, pp. 4539-4543.

K. Creath, "Phase-shifting speckle interferometry," Appl. Opt. 24, 1985, pp. 3053-3058.

H. Gundlach, "Phase contrast and differential interference contrast instrumentation and applications in cell, developmental, and marine biology," Opt. Eng. 32, 1993, pp. 3223-3228.

E. Cliche, F. Bevilacqua, and C. Depeursinge, "Digital Holography for quantitative phase-contrast imaging," Opt. Lett. 24, 1999, pp. 291-293.

C.K. Hitzenberger, M. Sticker, R. Leitgeb, and A.F. Fercher, "Differential phase measurements in low-coherence interferometry without $2\pi$ ambiguity," Opt. Lett. 26, 2001, pp. 1864-1866.

Hirwnvwefwe et al., "Overcoming the 2it ambiguity in low coherence interferometric differential phase measurements," Proc. SPIE, Coherence Domain Optical Methods in Biomedical Science and Clinical Applications, 2001, vol. 4251, pp. 81-85.

C. Yang, A. Wax, R.R. Dasari, and M.S. Feld, "$2\pi$ ambiguity-free optical distance measurement with subnanometer precision with a novel phase-crossing low-coherence interferometer," Opt. Lett. 27, 2002, pp. 77-79.

D.R. Lide, ed., "CRC Handbook of Chemistry and Physics," CRC Press, 2001-2002.

Ding et al., "Real-time phase-resolved optical coherence tomography and optical Doppler tomography," Optics Express, Mar. 2002, vol. 10 No. 5.

R. Tripathi, N Nassif, J. S. Nelson, B. H. Park, and J. F. De Boer, "Spectral shaping for non-Gaussian source spectra in optical coherence tomography," Opt. Lett. 27, 2002, pp. 406-408.

Westphal, Volker et al., "Correction of Geometric and Refractive Image Distortions in Optical Coherence Tomography Applying Fermat's Principle," Optics Express, May 6, 2002, pp. 397-404, vol. 10, No. 9.

J. Gass, A. Dakoff, and M. K. Kim, "Phase imaging without $2\pi$ ambiguity by multiwavelength digital holography," Opt. Lett. 28, 2003, pp. 1141-1143.

J.F. De Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 2003, pp. 2067-2069.

M. A. Choma, M. V. Sarunic, C. Yang, and J. A. Izatt, "Sensitivity advantage of swept source and Fourier domain optical coherence tomography," Opt. Express 11, 2003, pp. 2183-2189.

R. Leitgeb, C. K. Hitzenberger, and A. F. Fercher, "Performance of Fourier domain vs. time domain optical coherence tomography," Opt. Express 11, 2003, pp. 889-894.

Zawadzki, Robert J. et al., "Three-Dimensional Ophthalmic Optical Coherence Tomography With a Refraction Correction Algorithm," SPIE, 2003, vol. 5140.

D.L. Marks, P.S. Carney, and S.A. Boppart, "Adaptive spectral apodization for sidelobe reduction in optical coherence tomography images," J. Biomed. Opt. 9, 2004, pp. 1281-1287.

G. Popescu, L. P. Deflores, J.C. Vaughan, K. Badizadegan, H. Iwai, R. R. Dasari and M. S. Feld, "Fourier phase microscopy for investigation of biological structures and dynamics," Opt. Lett. 29, 2004, pp. 2503-2505.

Tang, Maolong, "Corneal Mean Curvature Mapping: Applications in Laser Refractive Surgery," Biomedical Engineering Center, 2004, Ohio State University.

C. Joo, T. Akkin, B. Cense, B. H. Park, and J. F. De Boer, "Spectral-domain optical coherence phase microscopy for quantitative phase-contrast imaging," Opt. Lett. 30, 2005, pp. 2131-2133.

C. J. Mann, L. Yu, C. Lo, and M. K. Kim, "High-resolution quantitative phase-contrast microscopy by digital holography," Opt. Express 13, 2005, pp. 8693-8698.

G. Popescu, T. Ikeda, C. A. Best, K. Badizadegan, R. R. Dasari, and M. S. Feld, "Erythrocyte structure and dynamics quantified by Hilbert phase microscopy," J. Biomed. Opt. 10, 2005, 060503.

M. A. Choma, A. K. Ellerbee, C. Yang, T. L. Creazzo, and J. A. Izatt, "Spectral-domain phase microscopy," Opt. Lett. 30, 2005, pp. 1162-1164.

T. Ikeda, G. Popescu, R. R. Dasari, and M.S. Feld, "Hilbert phase microscopy for investigating fast dynamics in transparent systems," Opt. Lett. 30, 2005, pp. 1165-1167.

M. A. Choma, A. K. Ellerbee, S. Yazdanfar, and J. A. Izatt, "Doppler flow imaging of cytoplasm streaming using spectral domain phase microscopy," J. Biomed. Opt. 11, 2006, 024014.

Sicam, Victor Arni D.P., "Spherical Aberration of the Anterior and Posterior Surfaces of the Human Cornea," J. Opt. Soc. Am. A, Mar. 2006, pp. 544-549, vol. 23, No. 3.

Tang, Maolong et al., "Measuring Total Corneal Power Before and After Laser in Situ Keratomileusis With High-Speed Optical Coherence Tomography," J. Cataract Refract Surg, Nov. 2006, pp. 1843-1850, vol. 32, No. 11.

A. K. Ellerbee and J.A. Izatt, "Phase retrieval in low-coherence interferometric microscopy," Opt. Lett. 32, 2007, pp. 388-390.

A. K. Ellerbee, T. L. Creazzo, and J. A. Izatt, "Investigating nanoscale cellular dynamics with cross-sectional spectral domain phase microscopy," Opt. Express 15, 2007, pp. 8115-8124.

E. J. McDowell, A. K. Ellerbee, M. A. Choma, B. E. Applegate, and J. A. Izatt, "Spectral domain phase microscopy for local measurements of cytoskeletal rheology in single cells," J. Biomed. Opt., 2007, 04400.

(56) References Cited

OTHER PUBLICATIONS

J. Kuhn, T. Colomb, F. Montfort, F. Charrière, Y. Emery, E. Cuche, P. Marquet, and C. Depeursinge, "Real-time dual-wavelength digital holographic microscopy with a single hologram acquisition," Opt. Express 15, 2007, pp 7231-7242.
N. Warnasooriya and M.K. Kim, "LED-based multi-wavelength phase imaging interference microscopy," Opt. Express 15, 2007, pp. 9239-9247.
Wang et al., "Three dimensional optical angiography." Optics Express, 2007, pp. 4083-4097, vol. 15 No. 7.
Wang, "Three-dimensional optical micro-angiography maps directional blood perfusion deep within microcirculation tissue beds in vivo," Phys. Med. Biol. 2007, pp. N531-N537, vol. 52.
N. Lue, W. Choi, G. Popescu, T. Ikeda, R. R. Dasari, K, Badizadegan, and M. S. Feld, "Quantitative phase imaging of live cells using fast Fourier phase microscopy," Appl. Opt. 46, 2007, pp. 1836-1842.
A. Khmaladze, A. Restrepo-Martínez, M.K. Kim, R. Castañeda, and A. Blandón, "Simultaneous Dual-Wavelength Reflection Digital Holography Applied to the Study of the Porous Coal Samples," Appl. Opt. 47, 2008, pp. 3203-3210.
D. L. Marks, S.C. Schlachter, A.M. Zysk, and S.A. Boppart, "Group refractive index reconstruction with broadband interferometric confocal microscopy," J. Opt. Soc. Am. A 25, 2008, pp. 1156-1164.
Erich Götzinger, Michael Pircher, Wolfgang Geitzenauer, Christian Ahlers, Bernhard Baumann, Stephan Michels, Ursula Schmidt-Erfurth, and Christoph K. Hitzenberger, "Retinal pigment epithelium segmentation by polarization sensitive optical coherence tomography," Opt. Express.
J.A. Izatt and M.A. Choma, "Theory of Optical Coherence Tomography," in Optical Coherence Tomography: Technology and Applications, W. Drexler and J.G. Fujimoto, eds, Springer, 2008.
R. M. Werkmeister, N. Dragostinoff, M. Pircher, E. Götzinger, C. K. Hitzenberger, R. A, Leitgeb, and L. Schmetterer, "Bidirectional Doppler Fourier-domain optical coherence tomography for measurement of absolute flow velocities in human retinal vessels," Opt. Lett. 33, 2008, pp. 2967-2969.
S. Tamano et al., "Phase-shifting digital holography with a low-coherence light source for reconstruction of a digital relief object hidden behind a light-scattering medium," Applied Optics, 2008,- pp. 953-959, vol. 45, No. 5, Optical Society of America.
Sarunic, Marinko et al., "Imaging the Ocular Anterior Segment With Real-Time, Full-Range Fourier-Domain Optical Coherence Tomography," Arch. Opthal., Apr. 2008, pp. 537-542, vol. 126, No. 4.
Vergnole et al., "Common Path swept source OCT interferometer with artifact removal." Proc of SPIE, 2008, 8 pages, vol. 6847.
V. Srinivasan, B.K. Monson, M. Wojtkowski, R.A. Bilonick, I. Gorczynksa, R. Chen, J.S. Duker, J.S. Schumann, J.G. Fujimoto, "Characterization of Outer Retinal Morphology with High-Speed, Ultrahigh Resolution Optical Coherence Tomography," Investigative Ophthalmology and Visual Science 49, 2008 pp. 1571.
H.C. Hendargo, M. Zhao, N. Shepard, and J.A. Izatt, "Synthetic wavelength based phase unwrapping in spectral domain optical coherence tomography," Opt. Express 17, 2009, pp. 5039-5051.
Hendargo et al., "Synthetic Wavelength-Based Phase Unwrapping in Fourier Domain Optical Coherence Tomography," Optics Express, 2009, pp. 5039-5051, vol. 17, Issue 7. http://dx.doi.org/10.1364/OE.17.005039.
Jae Ho Han et al., "Common path fourier domain optical coherence tomography in ophthalmology applications," Life Science Systems and Applications Workshop, 2009, pp. 163-166.
Zhao, Mingtao et al., "Single-Camera Sequential-Scan-Based Polarization-Sensitive SDOCT for Retinal Imaging," Optics Letters, Jan. 15, 2009, pp. 205-207, vol. 34, No. 2.
Liu et al. "Compressive SD-OCT: the application of compressed sensing in spectral domain optical coherence tomography," Optics Express, 2010, pp. 22010-22019, vol. 18, Issue 21.
Yogesh, Verma et al., "Use of common path phase sensitive spectral domain optical coherence tomography for refractive index measurements." Applied Optics, 2011, pp. E7-E12, vol. 50, Issue 25.
Park et al., "Double common-path interferometer for flexible optical probe of optical coherence tomography," Optics Express, 2012, pp. 1102-1112, vol. 20, Issue 2.
Uhlhorn et al., "Refractive Index Measurement of the Isolated Crystalline Lens Using Optical Coherence Tomography," Vision Research 48 (2008), pp. 2732-2738.
International Search Report and Written Opinion for Application No. PCT/US2010/033540 dated Jul. 16, 2010.
Non-Final Office Action for U.S. Appl. No. 12/386,945 dated Jul. 13, 2011.
Final Office Action for U.S. Appl. No. 12/386,945 dated May 23, 2012.
Non-Final Office Action for U.S. Appl. No. 12/460,532 dated Jul. 13, 2012.
Notice of Allowance for U.S. Appl. No. 12/460,532 dated Feb. 20, 2013.
Non-Final Office Action for U.S. Appl. No. 12/386,945 dated Mar. 19, 2013.
Notice of Allowance for U.S. Appl. No. 12/460,532 dated May 24, 2013.
Non-Final Office Action for U.S. Appl. No. 12/799,890 dated Aug. 9, 2013.
Notice of Allowance for U.S. Appl. No. 12/799,890 dated Nov. 19, 2013.
Notice of Allowance for U.S. Appl. No. 12/386,945 dated Jan. 29, 2014.

* cited by examiner

SYSTEMS AND METHODS FOR COMPLEX CONJUGATE ARTIFACT RESOLVED OPTICAL COHERENCE TOMOGRAPHY

RELATED APPLICATION

The presently disclosed subject matter claims the benefit of U.S. Provisional Patent Application Ser. No. 61/434,859, filed Jan. 21, 2011, the disclosure of which is incorporated herein by reference in its entirety.

GOVERNMENT INTEREST

This invention was made with U.S. Government support under Grant Nos. R21 EY019411 and R01 EY014743 awarded by the United States National Institutes of Health and Grant No. FA8650-09-C-7932 awarded by the Defense Advanced Research Projects Agency. Thus, the U.S. Government has certain rights in the invention.

TECHNICAL FIELD

The present disclosure relates generally to imaging systems such as optical coherence tomography systems. More particularly, the subject matter disclosed herein relates to systems and methods for complex conjugate resolved optical coherence (OCT) tomography.

BACKGROUND

OCT is a non-invasive imaging modality that provides micrometer scale resolution of tissue structures over depth ranges of a few millimeters. The technique has found a number of biomedical applications, most notably in ophthalmic and cardiovascular imaging.

Swept-source OCT (SSOCT) is an improvement to OCT that provides a dramatic sensitivity advantage over traditional time domain techniques. However, SSOCT suffers from an inherent (i.e. sample independent) reduced imaging depth range, typically limited to between 1 and 4 mm. Optical attenuation from absorption and scattering in tissue typically limit how much light is recovered from depths beyond a few millimeters, and thus for many applications this inherent reduced depth range is not the limiting factor in determining the practical imaging depth. However, several important OCT applications would benefit from extended imaging depths, including ophthalmic imaging of the anterior segment, small animal imaging, endoscopic imaging, and catheter imaging of coronary arteries.

Extending the imaging range of SSOCT has thus been an area of interest for which a number of techniques have been developed. However, all of these techniques are accompanied by drawbacks including reduced sensitivity, reduced axial resolution, reduced imaging speed, required lateral oversampling, increased system complexity, increased cost and/or increased signal processing overhead. In addition, many of these techniques produce incomplete suppression of the complex conjugate artifact, resulting in distracting "ghost" images.

SSOCT suffers from a limited inherent imaging depth range due to two factors. The first of these stems from the fact that SSOCT extracts depth information from the Fourier transform of a spectral interferogram. As the spectral interferogram can only be recorded as a real signal, its Fourier transform is necessarily Hermitian symmetric. Consequently, positive and negative displacements from the zero pathlength difference position (DC) cannot be unambiguously resolved, giving rise to mirror image artifacts. This phenomenon is termed the complex conjugate ambiguity. These artifacts can be avoided by placing the zero pathlength difference position outside of the sample, which results in two mirror images of the sample being acquired in the positive and negative frequencies. While this technique resolves the ambiguity between positive and negative displacements, it also effectively halves the useful imaging range of SSOCT systems, and may result in the appearance of "wrapped" mirror image artifacts if the sample moves unexpectedly.

The complex conjugate ambiguity would not pose such a problem if it were not for the fact that the total imaging range is also limited by a phenomenon known as sensitivity fall-off. The instantaneous linewidth of the swept laser in SSOCT systems (and the spectral bandwidth of each spectrometer pixel, in SDOCT systems) can be thought of as a sampling function that interrogates the intrinsic spectral interferogram. The spectral interferogram is sampled by, and thus convolved with, the laser linewidth (or spectrometer pixel bandwidth), which results in reduced fringe visibility when the fringe period is small. As smaller fringe periods (i.e. higher fringe frequencies) correspond to deeper imaging depths, this reduced visibility results in decreasing sensitivity with increasing imaging depth.

An effective method for resolving the complex conjugate ambiguity is heterodyne SSOCT (HSSOCT), which resolves the ambiguity by shifting the peak sensitivity position image away from DC, such that positive and negative displacements from that position can be discerned. As this technique shifts, rather than suppresses, the complex conjugate signal, it completely resolves the artifact. In addition, HSSOCT does not result in any reduction in imaging speed or require lateral oversampling. In this method, two frequency shifters, usually acousto-optic modulators (AOM's) (though electro-optic modulators (EOM's) have been used) are used to apply different modulation frequencies to the sample and reference arm. While effective, this technique is limited in that the modulators are expensive and difficult to implement. More significantly, AOM's tend to have appreciable insertion losses, resulting in reduced sensitivity, and also often restrict optical bandwidth, resulting in reduced axial resolution. In addition, processing of the acquired data requires either hardware demodulation or significant additional post-processing steps.

SUMMARY

In accordance with this disclosure, novel systems and methods for complex conjugate resolved OCT are provided. The systems and methods for complex conjugate resolved OCT disclosed herein improve imaging. For example and without limitation, the systems and methods for complex conjugate resolved OCT can double the usable imaging depth range in OCT, can allow for centering the highest signal-to-noise (SNR) portion of the image near the middle of the depth imaging range, and can also allow for depth multiplexing for the simultaneous imaging of multiple regions within a sample.

Some of the objects of the subject matter disclosed herein having been stated hereinabove, and which are achieved in whole or in part by the presently disclosed subject matter, other objects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

Figure 1:
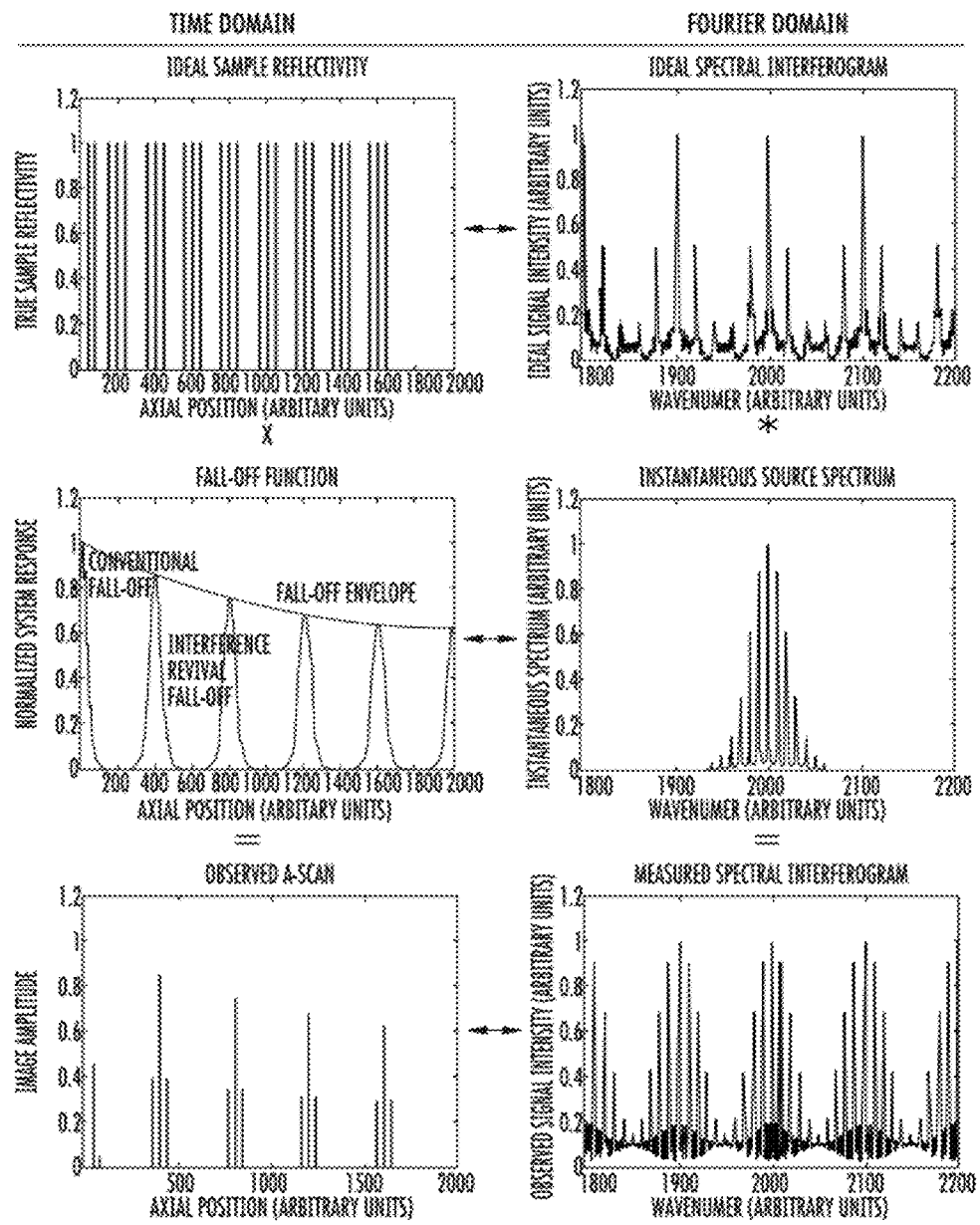
FIG. 1 provides graphs of embodiments of time and Fourier domain representations of coherence revival according to one embodiment of the presently-disclosed subject matter, wherein the ideal interferogram can be convolved with the instantaneous source spectrum to yield the measured spectral interferogram, which is the Fourier transform of an observed A-scan and, equivalently, the ideal sample reflectivity is multiplied by the fall-off function, resulting in the observed A-scan.

Reference will now be made in detail to possible aspects or embodiments of the subject matter herein, one or more examples of which are shown in the figures. Each example is provided to explain the subject matter and not as a limitation. In fact, features illustrated or described as part of one embodiment can be used in another embodiment to yield still a further embodiment. It is intended that the subject matter disclosed and envisioned herein covers such modifications and variations. As illustrated in the various figures, some sizes of structures or portions may exaggerated relative to other structures or portions for illustrative purposes and, thus, are provided to illustrate the general structures of the present subject matter.

Although the terms first, second, etc. may be used herein to describe various features, elements, components, regions, layers and/or sections, these features, elements, components, regions, layers and/or sections should not be limited by these terms. These terms are only used to distinguish one feature, element, component, region, layer or section from another feature, element, component, region, layer or section. Thus, a first feature, element, component, region, layer or section discussed below could be termed a second feature, element, component, region, layer or section without departing from the teachings of the disclosure herein.

Embodiments of the subject matter of the disclosure are described herein with reference to schematic illustrations of embodiments that may be idealized. As such, variations from the shapes and/or positions of features, elements or components within the illustrations as a result of, for example but not limited to, user preferences, manufacturing techniques and/or tolerances are expected. Shapes, sizes and/or positions of features, elements or components illustrated in the figures may also be magnified, minimized, exaggerated, shifted or simplified to facilitate explanation of the subject matter disclosed herein. Thus, the features, elements or components illustrated in the figures are schematic in nature and their shapes and/or positions are not intended to illustrate the precise configuration of a system or apparatus and are not intended to limit the scope of the subject matter disclosed herein.

Optical coherence tomography (OCT) enables non-invasive, micrometer scale imaging of biological tissues over depth ranges of a few millimeters, and has found widespread use in several biomedical imaging applications, especially ophthalmic and cardiovascular imaging. Fourier domain optical coherence tomography (FDOCT) techniques, including swept source OCT (SSOCT) and spectrometer-based or spectral-domain OCT both provide a dramatic sensitivity advantage over the traditional time-domain counterpart, and have recently been demonstrated at A-scans rates for SSOCT exceeding 1 MHz. Unfortunately, these techniques suffer from inherent limited imaging depth due to the so-called sensitivity fall-off effect (due to the finite coherence length of the lasers used in SSOCT and the finite pixel width of spectrometers in SDOCT) as well as the complex conjugate artifact, which together result in a typical maximum imaging range of about 1 mm to about 5 mm. While optical attenuation from absorption and scattering typically places an even more restrictive limit on the attainable imaging depth, there are several applications that would benefit from extended imaging depths, most notably ophthalmic imaging of the ocular anterior segment, intrasurgical imaging, and catheter imaging of coronary arteries.

The complex conjugate ambiguity arises from the fact that, in FDOCT, depth profiles of the sample are obtained from the Fourier transform of a spectral interferogram. Because the spectral interferogram is acquired as a real signal, its Fourier transform is always Hermitian symmetric. As a result, positive and negative displacements about the matched pathlength position cannot be distinguished. As the sensitivity of an SSOCT system decays with increasing distance from this matched pathlength position, the presence of the complex conjugate effectively halves the usable imaging range.

Resolving this ambiguity to double the FDOCT imaging depth is an area of interest for which a number of techniques have been developed. These techniques include phase shifting using a PZT-mounted reference arm or electro-optic phase modulator, heterodyne SSOCT (HSSOCT), instantaneous acquisition of phase separated interferograms using 3×3 interferometers or polarization encoding, harmonic lock-in detection of phase modulation, imparting a phase ramp across a B-scan with either B-M mode scanning or pivot-offset scanning, and dispersion encoding. The extended imaging range afforded by many of these techniques is accompanied by disadvantages, either in the form of reduced sensitivity, reduced axial resolution, reduced imaging speed, increased system complexity, increased cost and/or complex post-processing. Furthermore, most of these techniques provide only partial suppression of the complex conjugate artifact, which can result in distracting "ghost" images.

Of particular interest is heterodyne SSOCT (HSSOCT), which resolves the ambiguity by creating a frequency shift that moves the peak sensitivity position away from electronic DC, such that positive and negative displacements from that position can be discerned. A significant advantage of this technique is that it shifts the complex conjugate, rather than attenuating it, and thus does not result in distracting ghost images. Heterodyne SSOCT has previously been implemented by using acousto-optic modulators (AOM's) to apply a differential frequency shift between the sample and reference arms. The drawbacks of the technique mostly stem from the use of AOM's, in that they typically have large insertion losses and restricted optical bandwidths, which results in reduced imaging sensitivity and reduced axial resolution. Furthermore, data processing in traditional implementations of heterodyne SSOCT is significantly more complicated than in traditional SSOCT, requiring either hardware demodulation or complicated post-processing.

Systems and methods of realizing resolved complex conjugated OCT, including FDOCT, SSOCT, heterodyne SSOCT and heterodyne SDOCT, using coherence revival are described in further detail below. These systems and methods can exploit the fact that some light sources used for FDOCT or light sources in combination with resonator cavities can automatically produce a phase modulated signal when used in an interferometer whose arms are mismatched by an integer multiple of the laser's cavity length. These systems and methods can have a number of advantages over other OCT technologies, for example, but not limited to traditional AOM-based heterodyne SSOCT, in that they can be simple to implement, can cause no reduction of axial resolution, and can require little to no additional hardware beyond conventional OCT systems, such as, for example, a traditional SSOCT system or SDOCT system. An additional processing step can be used in the methods and systems that involve use of a numerical dispersion compensation algorithm, which is an ordinary processing step in many FDOCT systems. These systems and methods can also be used in some embodiment applications for simultaneous dual-depth SSOCT imaging of the anterior and posterior eye.

Coherence Revival

"Coherence revival" as used herein refers to the phenomenon where interference fringes are observed in an interferometer illuminated by a light source, which can include, but is not limited to having, a comb-like spectrum not only when the reference and sample arms are matched in delay, but also when the two arms are mismatched at periodic intervals. These intervals can be several orders of magnitude longer than the source coherence length. As used herein, "coherence revival" is generally considered synonymous with the phrase "interference revival" as the phrase is used in the optical arts.

This phenomenon of coherence revival can occur if, for example, a light source in an interferometer being used is a laser that is simultaneously oscillating at multiple longitudinal modes. The period at which each set of interference fringes is observed can be equal to the reciprocal of the mode spacing, which can also be equal to the roundtrip delay of the laser cavity. This phenomenon can be used to measure the mode spacing of multi-mode diode lasers.

Briefly, if such a laser oscillates at multiple longitudinal modes simultaneously, even if these modes have random phase relationships with respect to each other (i.e. the laser is not mode locked), the multi-mode field emitted from the laser can have a periodic waveform. This periodicity stems from the fact that the mode spacing is constant, or, equivalently, that the laser cavity length is fixed. The field outside the cavity can thus be periodic with a period equal to, or generally equal to, the roundtrip cavity delay.

The phenomenon of coherence revival can also occur if a light source in an interferometer is made to pass through an optical resonator cavity, such as for example a Fabry-Perot cavity, that exhibits a frequency comb-like filter function, such that the light exiting the resonator cavity also has a periodic waveform. Frequency comb-like filters can be accomplished in different ways. For example, and without limitation, comb-like filters can be used such as those disclosed in U.S. Pat. Nos. 7,602,500 and 7,990,541, both of which are incorporated by reference herein in their entireties.

Coherence Revival in SSOCT

Coherence revival can occur in some embodiments of SSOCT as many currently available and emerging commercial swept source lasers are external-cavity tunable lasers (ECTL's) that exhibit this behavior. These lasers can typically include a semiconductor gain chip inside an external cavity (typically tens of millimeters in length). The long cavity can provide very fine mode spacing, and, under certain conditions, several of these longitudinal modes can oscillate simultaneously. These lasers can sweep by employing a tunable filter, located inside the cavity, that can create large loss at all but a small subset of these modes. As the filter tunes, the laser will mode-hop between these finely spaced longitudinal modes, but because many of the finely spaced modes are excited simultaneously, the tuning appears smooth on a macro-scale.

A consequence of coherence revival is that interference fringes can be observed when the sample and reference arm are mismatched by an integer multiple of the laser cavity length. This effect can be understood as arising from the interference of sequential pulses emanating from a pulsed laser, where a first emitted pulse can travel through the reference arm, and a second emitted pulse can travel through a shorter sample arm. Both pulses arrive at the receiver simultaneously and with a high degree of mutual coherence. Therefore, by mismatching the interferometer arms by one cavity length, the optical path delay of the laser cavity is effectively applied in the sample arm. This concept can be extended to place any number of virtual cavities in the sample arm.

Phase Modulation in the Virtual Cavity

A consequence of this virtual cavity effect can be that the optical path delay of the cavity is effectively applied in the sample arm (under conditions of coherence revival). In an ordinary SSOCT system, effects such as dispersion and phase modulation that occur in the laser cavity are common to light propagating in both the sample and the reference arm, and thus do not affect the SSOCT signal. However, when coherence revival is used to place a virtual cavity in only one arm of the interferometer, this symmetry is broken, and the optical path delay of the cavity can be applied in the sample arm only. Thus, any dispersion or phase modulation that is created in the laser cavity will then affect the SSOCT signal.

One of the challenges of prior implementations of heterodyne SSOCT is that the AOM's used are expensive, lossy, dispersive, and difficult to implement. An advantage of the virtual cavity effect can be that it can allow for the placement of a phase modulator directly inside the laser cavity. It has been observed that at least two different models of commercially available swept source lasers can create phase modulation automatically when employed in a coherence revival configuration. The source of this phase modulation can be a frequency shift due to variation of the optical pathlength (OPL) of the laser cavity over the course of the laser sweep. This frequency shift can be due to a change in the physical length of the cavity, as part of the tuning mechanism, or a modulation of the refractive index of some element in the cavity, perhaps for example as would result from carrier-induced changes of the refractive index of the gain media.

To demonstrate mathematically how a variation in the laser cavity OPL results in phase modulation, an expression is derived for the SSOCT signal in a system where the OPL difference between the reference and the sample varies during the scan. The interferometric cross term of the SSOCT signal in a system where the length of one arm changes over the course of the sweep is described by:

$$i_n(t) \propto \cos(2k(t)[z_r - z_n(t)]) \quad (1)$$

where $i_n(t)$ is the time dependent photocurrent due to the $n^{th}$ sample reflector, $k(t)$ is the wavenumber that is swept in time, and $z_r$ and $z_n(t)$ are the axial positions of the reference mirror and $n^{th}$ reflector. The axial position of the sample reflector is allowed to vary in time during the sweep.

An initial assumption is that the change in the cavity OPL varies linearly with the instantaneous central wavelength of the laser sweep, $\lambda_c$. The reflector position can then be cast as a function of $\lambda_c$:

$$z_n(\lambda_c) = z_{n0} + M(\lambda_0 - \lambda_c) \quad (2)$$

where $\lambda_0$ is the central wavelength of the sweep, $z_{n0}$ is the mean position of the $n^{th}$ sample reflector, and M is a parameter that describes the slope of the OPL change with wavelength (e.g. in mm/nm). Equation 1 and Equation 2 can be combined and thus the photocurrent can be recast as a function of the instantaneous central wavenumber, $k_c$, to yield:

$$i_n(k_c) \propto \cos(2k_c(z_r - z_{n0} - M\lambda_0) + 4\pi M) \quad (3)$$

Here, the $M\lambda_0$ term represents the axial position shift produced by the phase modulation, and the $4\pi M$ term is a constant and unimportant phase shift. Thus, the axial position shift created by the cavity length variation, $\Delta z$, can be expressed as:

$$\Delta z = M\lambda_0 \quad (4)$$

It is important to note that this axial position shift is created as a phase delay only. Group delay is given by the derivative of the instantaneous phase shift with respect to frequency, and although the laser cavity OPL changes over the course of the sweep, the cavity length is constant with respect to optical frequency at all times during the sweep. Thus, the cavity OPL variation creates a phase delay without creating an offsetting group delay. This separation between phase and group delay enables the separation between the real image and its complex conjugate.

Coherence Revival in the Fourier Domain

The preceding treatment does not address the reduced visibility of interference fringes observed in coherence revival. This loss of visibility is understood by considering coherence revival in the Fourier domain. The length and finesse of the Fabry-Perot resonator cavity determine the spacing and spectral purity of the resonator modes, respectively. The transmission function of the resonator is given by:

$$T_{cavity}(\omega) = \frac{T_{max}}{1 + \left(\frac{2F}{\pi}\right)^2 \sin^2\left(\frac{\pi\omega}{\omega_{FSR}}\right)} \quad (5)$$

where $T_{max}$ is the peak spectral density, F is the cavity finesse, and $\omega_{FSR}$ is the angular free spectral range given by $\omega_{FSR} = \pi c / n_{eff} L$. Assuming the laser has at least moderate finesse, (F>5), this expression is well approximated by a series of Lorentzian functions, i.e. a Lorentzian convolved with a comb:

$$T_{cavity}(\omega) \approx \left(\frac{T_{max}}{1 + (\tau\omega)^2}\right) * \left(\sum_{m=-\infty}^{\infty} \delta(\omega - m\omega_{FSR})\right) \quad (6)$$

where $\tau$ is given by $\tau = 2F/\omega_{FSR}$ and is inversely proportional to the linewidth of the Lorentzian, and $\delta$ denotes the Dirac delta function. The ECTL can also have a tunable filter placed inside the cavity, with a passband that is much broader than the mode spacing, such that many modes can oscillate simultaneously. If the transmission function of the tunable filter is denoted as $T_{filter}$, the instantaneous spectrum of this type of laser can be expressed as:

$$S_{inst}(\omega, \omega_c) = S_{source}(\omega) T_{filter}(\omega, \omega_c) \left[ \left( \frac{T_{max}}{1 + (\tau\omega)^2} \right) * \left( \sum_{m=-\infty}^{\infty} \delta(\omega - m\omega_{FSR}) \right) \right] \quad (7)$$

where $S_{source}(\omega)$ is the integrated power spectral density of the laser sweep, and $T_{filter}$ also depends on $\omega_c$, the instantaneous central frequency of the laser that varies over sweep.

For each spectral channel of an SSOCT A-scan centered at a frequency $\omega_c$, the detected photocurrent is equal to ideal spectral interferogram multiplied by the instantaneous spectrum $S_{inst}(\omega,\omega_c)$ and then integrated over $\omega$. This is analogous to convolving the ideal spectral interferogram with the instantaneous spectrum, and thus the sensitivity fall-off profile is related to the Fourier transform of the instantaneous spectrum. For simplicity, it is assumed that $T_{filter}$ maintains a constant shape across the sweep, and thus the magnitude of its Fourier transform is constant. The fall-off profile is then given by directly taking the normalized magnitude of the Fourier transform of Equation 7 with respect to $\omega$, and recasting in terms of the pathlength mismatch, z:

$$f_{falloff}(z) = f_{filter}(z) * \left[ \exp\left( -\frac{|z|}{\zeta} \right) \left( \sum_{m=-\infty}^{\infty} \delta(z - mn_{eff}L) \right) \right] \quad (8)$$

where $z=tc/2$, L is the physical cavity length, $n_{eff}$ is the effective refractive index, $\zeta$ is the characteristic decay distance given by $\zeta=n_{eff}LF/\pi$, and $f_{filter}$ is the Fourier transform of $T_{filter}$. Because the source bandwidth is much broader than the filter's spectral bandwidth, after Fourier transformation, the contribution of the source to the fall-off profile is negligible and has thus been dropped.

The fall-off profile in Equation 8 is composed of a comb with a period $n_{eff}L$ that is multiplied by a double-sided exponential function with a characteristic decay distance $\zeta$. The comb is then convolved with $f_{filter}$, which is the magnitude of the Fourier transform of the tunable filter passband. As with conventional SSOCT, $f_{filter}$ defines the SSOCT fall-off profile. For coherence revival, this profile applies to each set of fringes, which are separated by the period of the comb. The exponential function, heretofore referred to as the coherence revival fall-off envelope, determines the loss of fringe visibility at increasing multiples of the cavity length. These relationships are all depicted in FIG. 1.

Conventional fall-off profiles are typically specified by the pathlength mismatch that results in a 6 dB loss in sensitivity. For comparison, the characteristic distance at which this envelope is reduced by the same amount is derived:

$$\Delta z_{-6\,dB} \approx 0.44 n_{eff} LF \quad (9)$$

This result suggests that, for ideal cavities with large finesse, the coherence revival fall-off envelope would allow the use of many cavity length offsets before fringe visibility is severely degraded.

Sampling and Digitization Considerations

The benefits of a coherence revival HSSOCT system require a sufficiently high digitization (sampling) rate to be fully realized. As HSSOCT functions by separating the positive and negative frequency components of the spectral interferogram, the OCT image is shifted in depth by an amount equal to $\Delta z$ (defined in Equation 4). As the deepest imaging depth that an SSOCT can resolve is related to the digitization rate, the digitization rate may need to be increased to resolve the extending depths afforded by the coherence revival HSSOCT system.

Non-Linear Cavity Length Variation

A consideration that has not yet been addressed relates to the assumption that the cavity OPL changes linearly with wavelength. Equation 3 demonstrates that such a linear relationship would result in a pure phase modulation. In practice, however, the OPL change may not be linear in wavelength, and may instead exhibit a non-linear relationship. This non-linear relationship would result in different wavelengths experiencing different OPL's in the sample arm, a phenomenon that is closely related to material dispersion. Thus, a non-linear OPL change with respect to wavelength would still create phase modulation, but with additional distortion in the axial point spread function (PSF) analogous to the effects of group velocity dispersion (GVD) and higher order dispersion. Fortunately, the well-established numerical techniques used to correct dispersion in FDOCT can also be used to correct this PSF distortion.

Detailed Methodology

Figure 2A:
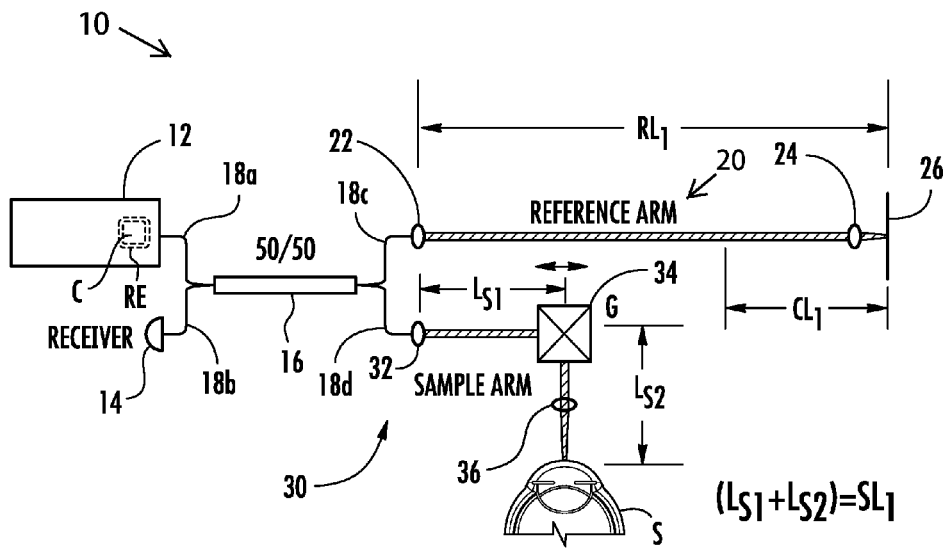
FIGS. 2A and 2B illustrate schematic views of embodiments of SSOCT systems according to other embodiments of the presently-disclosed subject matter.

Different types of systems, such as for example and without limitation SSOCT systems, can be used to perform coherence revival heterodyne FDOCT. For example, FIG. 2A illustrates a basic schematic of an embodiment of a coherence revival based FDOCT system, in the form of an SSOCT system, generally designated 10, employing a simple Michelson fiber interferometer according to the present subject matter. SSOCT system 10 can comprise a light source 12, a receiver 14, a beam splitting device, such as a fiber coupler 16, a reference arm, generally designated 20, and a sample arm, generally designated 30. A resonator cavity C can be provided through which light from light source 12 can travel and in which a phase modulation of the light can occur as the light travels through the resonator cavity. The resonator cavity can be a part of the light source 12 or can be separate from and/or external to light source 12. For example, in some embodiments, resonator cavity C can be defined in a resonator RE, which can be in a housing in which the light source resides.

Light source 12 can comprise a laser. For example, light source 12 can comprise an external cavity tunable laser within an external resonator RE in which a laser medium can be defined or a laser in which a resonator cavity is an integral and internal component of the laser. In some embodiments, the laser can have a slope of a cavity length variation that is adjustable to control axial position shift to allow a linear-in-wavelength cavity length variation.

Light source 12 and a receiver 14 that serves as a detector can be connected to a fiber coupler 16 by optical fibers 18a and 18b. An optical circulator (not shown) can be used to direct light from light source 12 to fiber coupler 16, and light returning from the fiber coupler to an input optical fiber (not shown) of receiver 14. Fiber coupler 16 can comprise two output optical fibers 18c and 18d. Reference arm 20 can comprise a collimating lens 22, a focusing lens 24, and a reference reflector 26 for reflecting a reference light portion provided by optical fiber 18c. Reference arm 20 can have an optical pathlength $RL_1$ between collimating lens 22 and reference reflector 26. Sample arm 30 can comprise a collimating lens 32, an aiming reflector, such as a galvanometer 34, a focusing lens 36, for focusing sample light portion on a sample S. Sample arm 20 can have an optical pathlength $SL_1$ that can comprise an optical pathlength $L_{S1}$ between collimating lens 32 and galvanometer 34 and an optical pathlength $L_{S2}$ between galvanometer 34 and sample S.

The reference arm optical pathlength and the sample arm optical pathlength can be offset from each other by an integer multiple of an optical pathlength of the resonator cavity. As shown in the embodiment in FIG. 2A, reference arm optical pathlength $RL_1$ can be longer than sample arm optical pathlength $SL_1$ by $CL_1$, which in the shown embodiment can be the same length of the optical pathlength of the resonator cavity. Thereby, reference arm optical pathlength $RL_1$ can be longer than sample arm optical pathlength $SL_1$ by $CL_1$, which can be an integer multiple of one (1) of the optical pathlength of the resonator cavity.

As shown in FIG. 2A, light from light source 12 can be sent to fiber coupler 16 via optical fiber 18b. Fiber coupler 16 can split the light from light source 12 into a reference light portion that can be transmitted through optical fiber 18c to reference arm 20 and a sample light portion that is transmitted through optical fiber 18d to sample arm 30. The reference light portion passes through collimating lens 22 and focusing lens 24 and reflects off reference reflector 26. The sample light portion passes through collimating lens 32 and focusing lens 34 and reflects off sample S. Light reflected from reference reflector 26 and sample S travels back through respective optical fiber 18c and optical fiber 18d through fiber coupler 16 and is sent to the receiver 14 via optical fiber 18b. As described previously, an optical circulator (not shown) can be used to direct the reflected light portions from fiber coupler 16 to receiver 14 via a different optical fiber. Due to the phase modulation generated in the resonator cavity and the difference between the optical pathlengths $RL_1$ and $SL_1$ that is an integer multiple of an optical pathlength of the resonator cavity, the reflected reference light portion from reference reflector 26 can be out-of-phase with the reflected sample light portion from sample S. Receiver 14 can calculate the difference between the out-of-phase reflected light in the optical fibers 18c, 18d. If, for example, the reflected reference light portion from reference reflector 26 and the reflected sample light portion from sample S are 180 degrees out-of-phase with one another, the interference components of the resulting signal will be twice that of the reflected light portions. The calculated different can then be used to separate positive displacement and negative displacement of complex conjugate components of an OCT interferogram. In this manner, the phase modulation of the light that is generated in the resonator cavity can be used to separate a positive and a negative displacement of a complex conjugate component of the OCT interferogram.

Figure 2B:
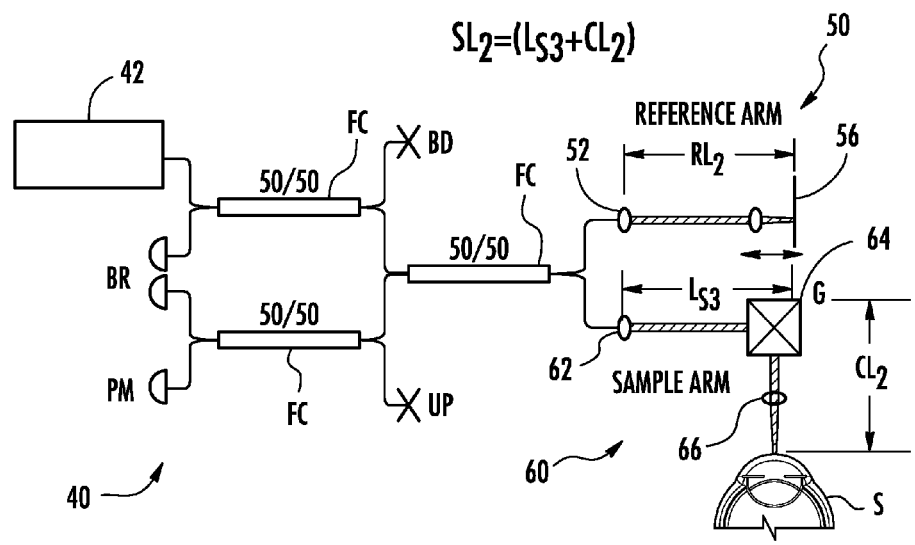

FIG. 2B illustrates another embodiment of a coherence revival based FDOCT system, in the form of an SSOCT system, generally designated 40, employing a spectrally balanced Michelson fiber interferometer according to the present subject matter. SSOCT system 40 can, for example and without limitation, comprise a light source 42, a balanced receiver BR, multiple beam splitting devices, such as 50/50 fiber couplers FC, arranged in an appropriate configuration, a power meter PM, a beam dump BD and unused port UP. The configuration and detailed operation of these components of SSOCT system 40 will not be described in more detail here since such a configuration is generally known in the art through the configuration and operation of a conventional spectrally balanced Michelson fiber interferometer.

SSOCT system 40 can also comprise a reference arm, generally designated 50, and a sample arm, generally designated 60. A resonator cavity can be provided through which light from light source 42 can travel and in which a phase modulation of the light can occur as the light travels through the resonator cavity. The resonator cavity can be a part of the light source 42 or can be separate from and/or external to light source 42. Reference arm 50 can comprise a collimating lens 52, a focusing lens 54, and a reference reflector 56 for reflecting a reference light portion back through the fiber couplers. Reference arm 50 can have an optical pathlength $RL_2$ between collimating lens 52 and reference reflector 56. Sample arm 60 can comprise a collimating lens 62, an aiming reflector, such as a galvanometer 64, a focusing lens 66, for focusing sample light portion on a sample S. Sample arm 60 can have an optical pathlength $SL_2$ that can comprise an optical pathlength $L_{S3}$ between collimating lens 62 and galvanometer 64 and an optical pathlength $CL_2$ between galvanometer 64 and sample S.

The reference arm optical pathlength and the sample arm optical pathlength can be offset from each other by an integer multiple of an optical pathlength of the resonator cavity. As shown in the embodiment in FIG. 2B, however, sample arm optical pathlength $SL_1$ can be longer than reference arm optical pathlength $RL_1$ by $CL_2$, which in the shown embodiment can be a length that is an integer multiple (i.e., one (1), two (2), three (3), etc.) of the optical pathlength of the resonator cavity.

Light reflected from reference reflector 56 of reference arm 50 of a reference light portion of light produced in light source 42 and light reflected from sample S of reference arm 60 of a reference light portion of light produced in light source 42 travels back through the respective fiber couplers FC and is sent to balanced receiver BR. As above, due to the phase modulation generated in the resonator cavity and the difference between optical pathlengths $RL_1$ and $SL_1$ that is an integer multiple of an optical pathlength of the resonator cavity, the reflected reference light portion from reference reflector 56 can be out-of-phase with the reflected sample light portion from sample S. Balanced receiver BR can calculate the difference between the out-of-phase reflected light. The calculated different can then be used to separate positive displacement and negative displacement of complex conjugate components of an OCT interferogram. In this manner, the phase modulation of the light that is generated in the resonator cavity can be used to separate a positive and a negative displacement of a complex conjugate component of the OCT interferogram.

Examples Using SSOCT Systems

SSOCT Systems Operating at 840 nm and 1040 nm

To demonstrate coherence revival heterodyne SSOCT in practice, two SSOCT systems have been constructed using different commercially available ECTL's. The first SSOCT system used a Thorlabs SL850-P16 tunable laser, produced by Thorlabs, Inc., headquartered in Newton, N.J. The Thorlabs SL850-P16 tunable laser had a central wavelength of about 840 nm, tuning bandwidth of 80 nm, and repetition rate of about 8 kHz (forward sweep only). The balanced receiver used was a Thorlabs PDB120A, a Silicon (Si) receiver with 75 MHz electronic bandwidth.

The second system used an Axsun Technologies swept source laser with a central wavelength of about 1040 nm, tuning bandwidth of about 100 nm and repetition rate of about 100 kHz produced by Axsun Technologies, Inc., headquartered in Billerica, Mass. The balanced receiver used in the 1040 nm system was a Wieserlabs WL-BPD1GA, an indium gallium arsenide (InGaAs) receiver with about 1 GHz electronic bandwidth produced by Wieserlabs UG located in Munich, Germany. An Alazar Technologies ATS9870 digitizer, produced by Alazar Technologies, Inc., located in Pointe-Claire, Quebec, Canada, was used for both systems, operating at 250 MS/s and 1 GS/s for the 840 nm and 1040 nm systems, respectively. Both systems can have identical topologies, and can make use of a spectrally balanced interferometer configuration. While the fiber couplers and detectors can differ between the two systems, the same digitizer and reference and sample arm optics can be used. A very long motorized translator, for example, a SGSP46-400X motorized translator produced by Sigma Koki headquartered in Tokyo, Japan, can be used in the reference arm. Both systems are similar to the system shown in FIG. 2B.

Sensitivity and fall-off measurements were made with both systems with the sample arms matched, and at various cavity length offsets. The cavity length of each laser was measured by placing an attenuated mirror in the sample arm and translating the reference arm over its entire linear travel (about 400 mm). The distance between the peak fringe visibility positions of each set of interference fringes was determined to be the cavity length. As used herein, the terms +1 or −1 cavity length offset are used to refer to the situations in which the sample arm was longer or shorter than the reference arm by an integer multiple of one (1) of the cavity optical pathlength, respectively.

For the 840 nm source, fall-off measurements were taken with cavity length offsets of −2, −1, 0, +1 and +2. For the 1040 nm source, only the −1, 0 and +1 cavity length offsets were used, because the phase modulation imparted by −2 and +2 offsets exceeded the electronic bandwidth of the digitizer. For each system, fall-off measurements were made using consistent levels of sample and reference power across all cavity lengths offsets, to allow the relative signal levels to be compared.

Finally, to demonstrate the feasibility of this technique for in vivo imaging, the ocular anterior segments of healthy human volunteers were imaged. For these experiments, the powers incident on the patient cornea were 600 μW and 1.8 mW for the 840 nm and 1040 nm systems, respectively, which were within the limits of the ANSI Z136.1 standard. To demonstrate the improved imaging depth with coherence revival CCR, both systems were used at both 0 and +1 cavity offsets. The sample arm used comprised two galvanometers (Cambridge technologies) and a compound objective lens designed to provide sufficient depth of field to demonstrate the extended imaging range of the SSOCT systems.

Wavenumber Recalibration and Dispersion Compensation

As the SSOCT signal was sampled linearly in time, and the lasers swept non-linearly in wavenumber, the acquired signal required resampling before Fourier transformation. Both lasers contained an internal Mach-Zehnder interferometer clock, whose signal was digitized along with the photoreceiver signal. The zero-crossings of the clock were detected and used to generate a linear-in-wavenumber recalibration vector that was used to resample the SSOCT signal linearly in wavenumber. However, because the clock signals were only intended for imaging depths of about 2.9 mm and about 3.7 mm (for the 840 nm and 1040 nm systems, respectively), the recalibration vector was first interpolated to increase the achievable imaging depth to about 9.4 mm and about 12.4 mm, respectively. The photoreceiver signals were then resampled using this recalibration vector via linear interpolation.

Dispersion from unmatched optics and fiber lengths in the sample and reference arm, as well as dispersion-like effects due to the non-linear-in-wavelength cavity length variation, can be corrected using numerical compensation. Briefly, after resampling to linearize the spectral interferogram in wavenumber, the spectral interferogram was multiplied by a complex "phase function", given by:

$$DC(k)=\exp(-j(a_1(k-k_0)^2+a_2(k-k_0)^3)) \quad (10)$$

where $a_1$ and $a_2$ are fitting parameters and $k_0$ is the central wavenumber of the sweep. Optimal values of $a_1$ and $a_2$ were determined using an optimization algorithm to maximize the peak signal from a mirror.

Results

Experimental Fall-Off Measurements

Figure 3A:
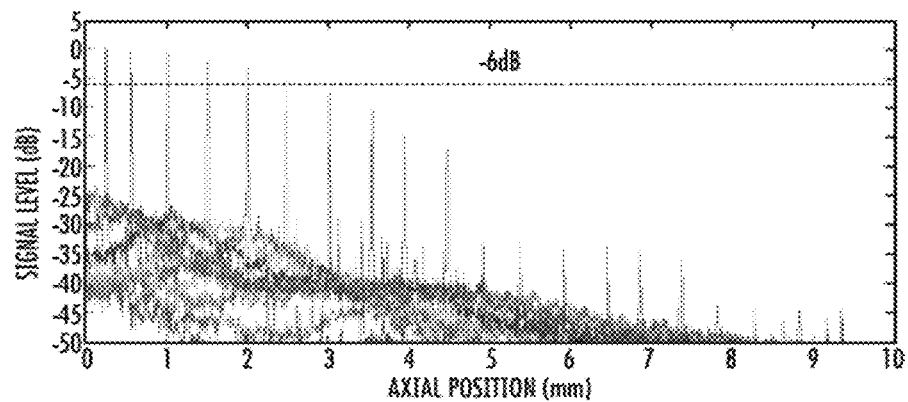
FIGS. 3A-3C illustrate graphs of fall-off measurements from a 840 nm system for 0 (FIG. 3A), +1 (FIG. 3B) and +2 (FIG. 3C) cavity length offsets according to embodiments of the presently-disclosed subject matter.
Figure 3B:
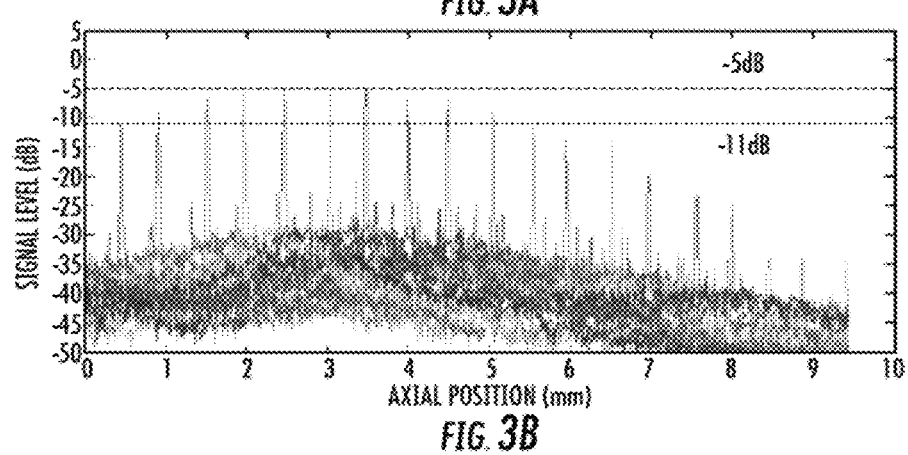
Figure 3C:
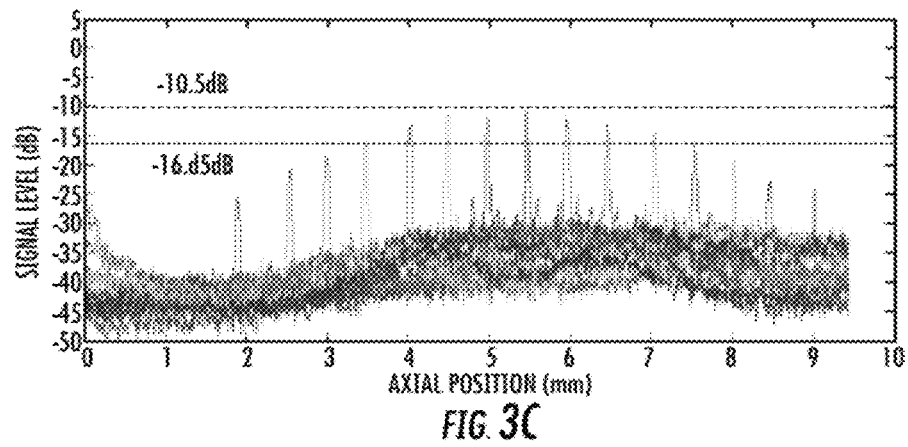

Fall-off profiles from the 840 nm system are shown in FIGS. 3A-3C. Results are shown for the 0 cavity offset (left) in FIG. 3A, +1 cavity offset (middle) in FIG. 3A, and +2 cavity offset (right) in FIG. 3A. Measurements at −1 and −2 cavity offsets were also made, but the results have been omitted here as they were nearly identical to the results from +1 and +2 offsets, respectively. The physical pathlength difference between the peak visibility positions of the 0 and +1 offsets was about 66.1 mm. The physical pathlength difference between the peak visibility positions of the 0 and +2 offset was precisely double (within the resolution of the translation stage), at about 132.2 mm. Exactly the same distances were observed for the negative offsets. These measurements were in good agreement with the manufacturer's estimate of the cavity length as approximately 50 mm of physical pathlength, without accounting for refractive index.

Figure 4A:
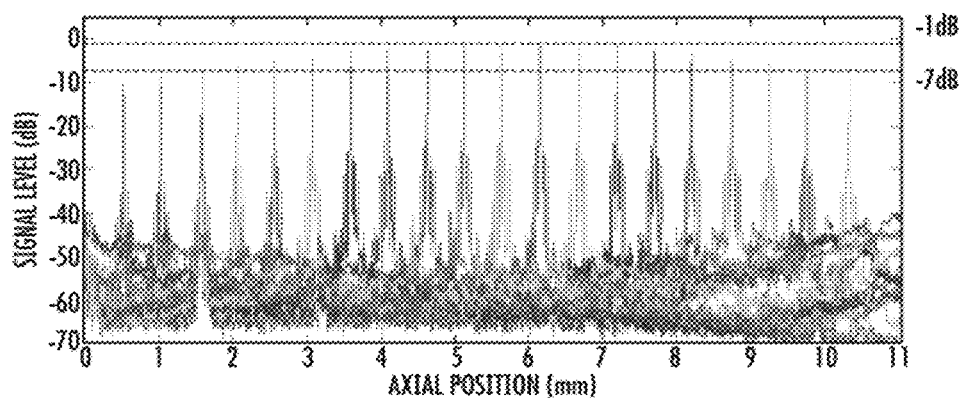
FIG. 4A-4C illustrates graphs of fall-off measurements from a 1040 nm system for −1 (FIG. 4A), 0 (FIG. 4B) and +1 (FIG. 4C) cavity length offsets, wherein the physical separations between the peak sensitivity positions of the −1 and 0 and the 0 and +1 offsets were about 115.0 mm and about 114.8 mm, respectively, according to embodiments of the presently-disclosed subject matter.
Figure 4B:
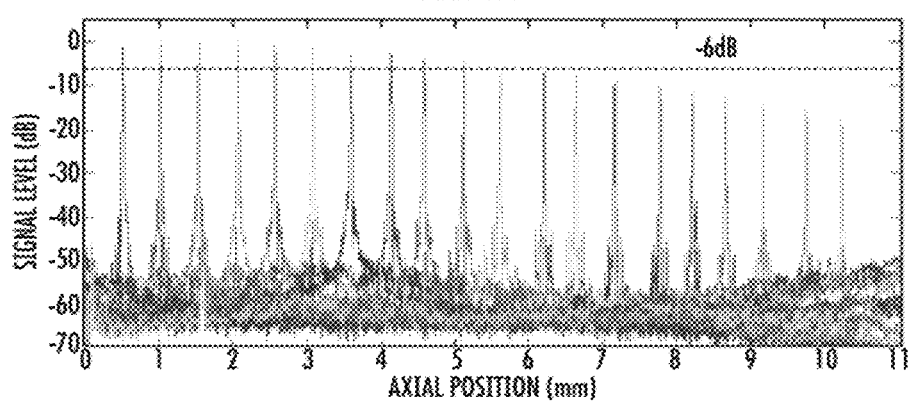
Figure 4C:
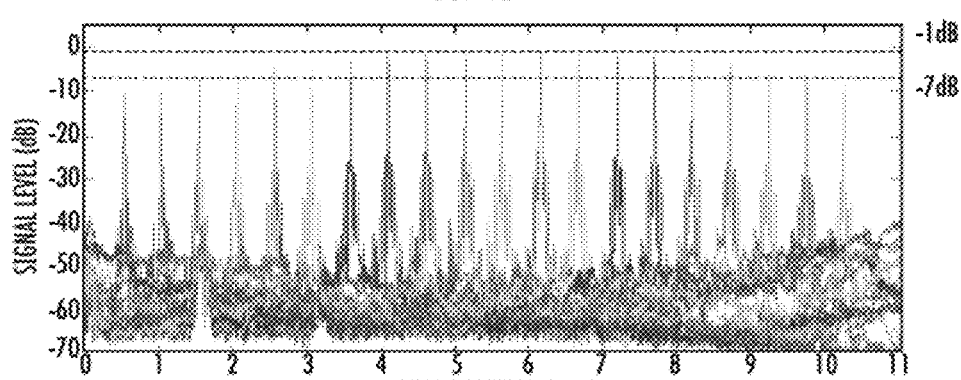

Fall-off profiles from the 1040 nm system are shown in FIGS. 4A-4C. Results are shown for the −1 cavity offset in FIG. 4A, 0 cavity offset in FIG. 4B and +1 cavity offset in FIG. 4C. The physical pathlength difference between the −1 and 0 and the 0 and +1 offsets were about 115.0 nm and about 114.8 mm, respectively. The variance in these two measurements was smaller than the specified repeatability of the translation stage. Again, this was in good agreement with the pathlength suggested by the manufacturer of approximately 80 mm of fiber.

Because the sample and reference powers were kept constant during these measurements, the loss in peak sensitivity for each cavity length offset can be determined from the falloff profiles. FIGS. 3B and 3C shows that the peak sensitivity in the +1 and +2 offsets for the 840 nm system were attenuated by ~5 dB and ~10.5 dB, respectively, from that of the pathlength matched case. If the usable imaging range can be defined as the depths over which the signal strength is reduced by less than 6 dB, the imaging ranges for the 840 nm were approximately 2.5 mm, 5 mm and 4 mm for the 0, +1 and +2 offsets.

Similarly, FIGS. 4A and 4C shows that the loss in sensitivity at the −1 and +1 offsets was only about 1 dB, despite the considerably longer cavity length. From this, it can be inferred that the finesse of the 1040 nm laser was much higher than the finesse of the 840 nm laser. The usable imaging ranges were about 9 mm, about 5.5 mm and about 9 mm for the −1, 0, and +1 offsets, respectively.

The optimal dispersion compensation phase functions were nearly identical between the +1 and −1 cavity length offsets for both systems. Furthermore, the phase function parameters $a_1$ and $a_2$ used to optimally correct measurements from −2 and +2 cavity length offsets (for the 840 nm system) were precisely double that of the phase function used for the −1 and +1 cavity length offsets.

Imaging Results

Figure 5:
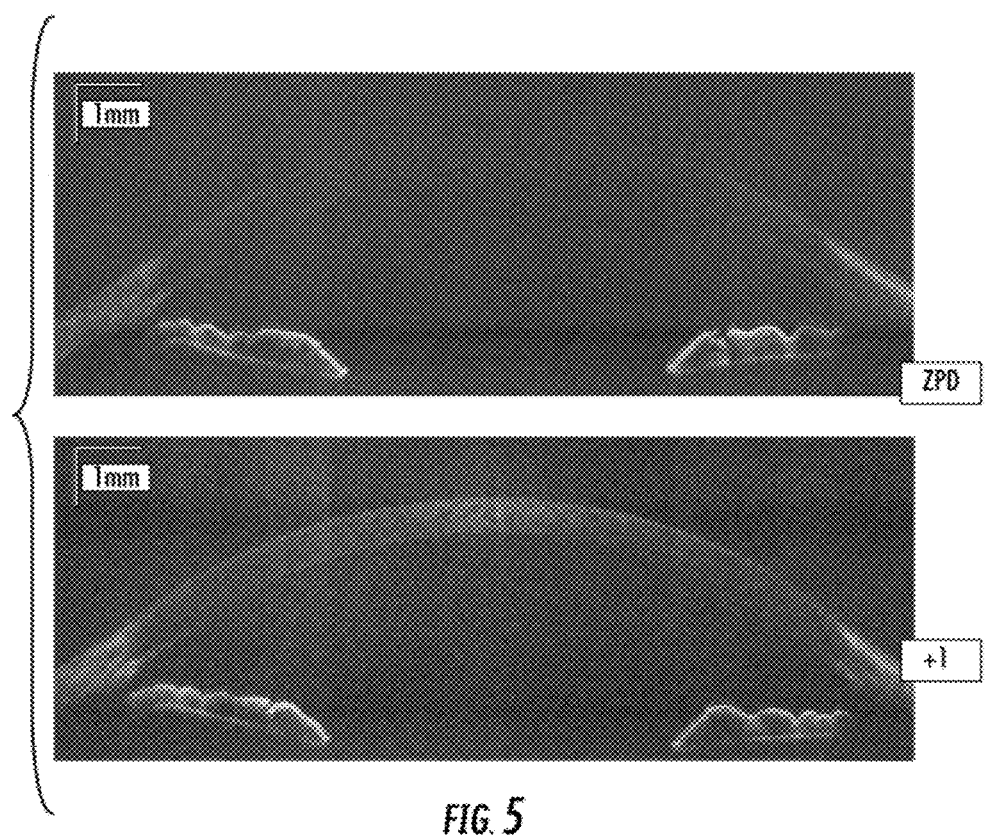
FIG. 5 illustrates comparison images taken on the 840 nm system with 0 (top) and +1 (bottom) cavity length offsets according to an embodiment of the presently-disclosed subject matter.
Figure 6:
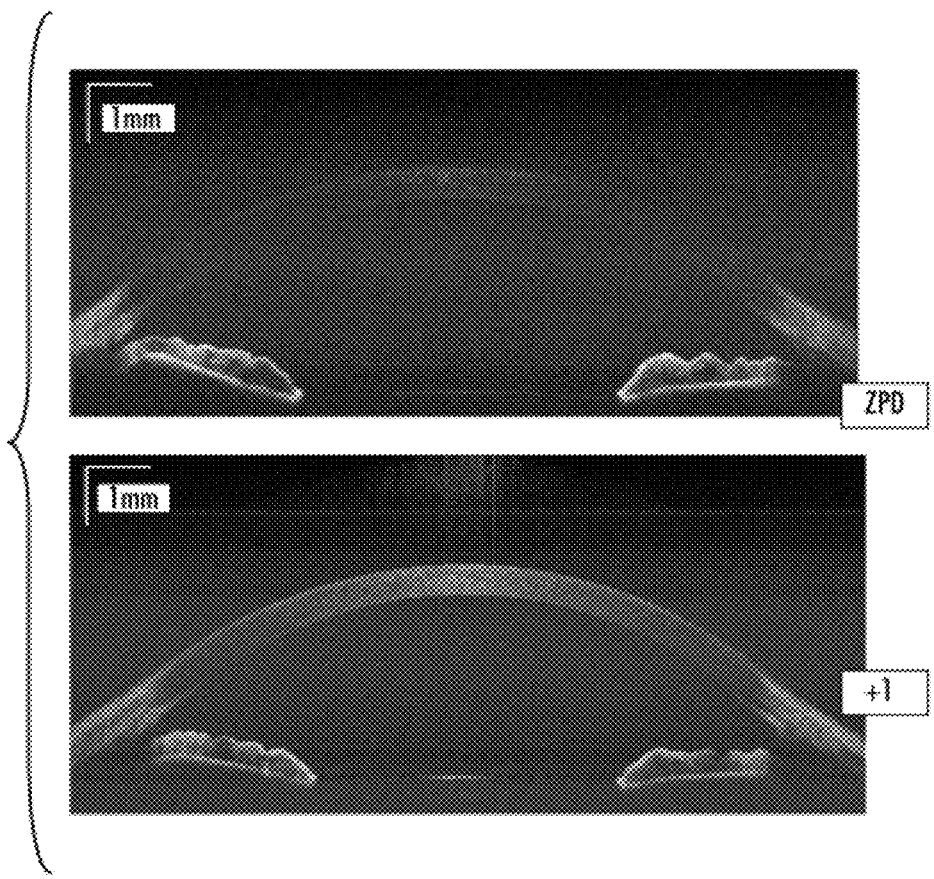
FIG. 6 illustrates comparison images taken on the 1040 nm system with 0 (top) and +1 (bottom) cavity length offsets according to an embodiment of the presently-disclosed subject matter.
Figure 7A:
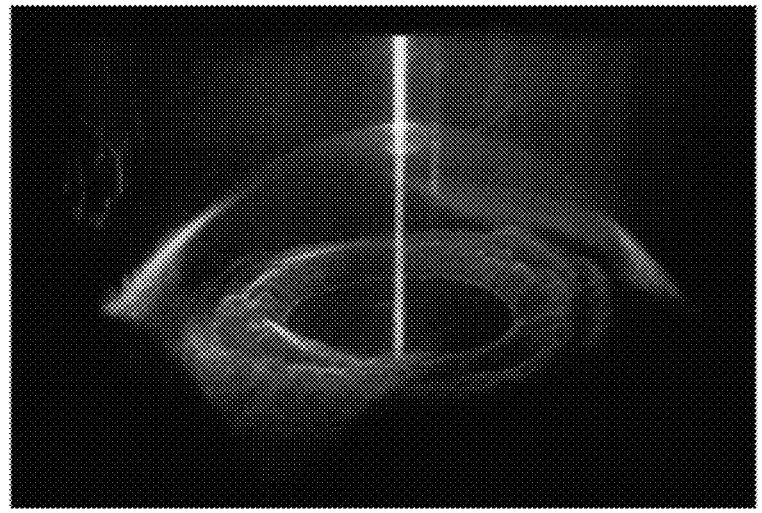
FIG. 7A illustrates a volume projection image of an eye acquired with the 840 nm according to an embodiment of the presently-disclosed subject matter.
Figure 7B:
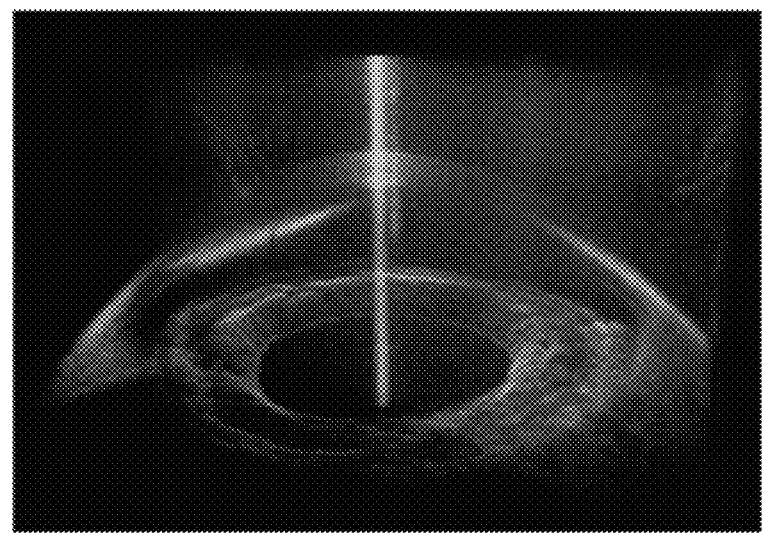
FIG. 7B illustrates a volume projection image of the same eye as the image of the volume projection in FIG. 7A acquired with the 1040 nm (14B) systems according to an embodiment of the presently-disclosed subject matter.

FIG. 5 shows the results of two images of a volunteer's ocular anterior segment for comparison. The image on the top was taken with the reference and sample arms matched in pathlength, whereas the image on the bottom was taken with the sample arm one cavity length longer than the reference arm. Both images were acquired on the 840 nm system, and each image comprises five averaged frames. The locations of the zero pathlength difference (ZPD) position and the +1 offset position are indicated. Both images comprise about 1000 (lateral)×about 1300 (axial)×about 5 (averaged frames) and have been scaled to account for refractive index and each image is acquired in about 0.6 seconds. FIG. 6 shows the results of the same experiment conducted on the 1040 nm system. Both images comprise about 2000 (lateral)×about 2300 (axial)×about 5 (averaged frames) and have been scaled to account for refractive index and each image is acquired in about 100 msec with the locations of the ZPD and +1 offset positions indicated. FIGS. 7A and 7B show two volume projections taken on the same eye with both the 840 nm (FIG. 7A) and 1040 nm (FIG. 7B) systems. In FIG. 7A, the 840 nm volume comprises about 1300 (axial)×about 500×about 200 samples, acquired in about 12.5 seconds. In FIG. 7B, the 1040 nm volume comprises about 2304 (axial)×about 500×about 200 samples, acquired in about 1 second.

The use of coherence revival is an implementation of heterodyne SSOCT and carries with it a number of advantages over traditional methods employing AOM's or EOM's. First and foremost, the method can be simple and inexpensive. For example, in cases where the laser already exhibits phase modulation, all that is required is an adjustment to the reference arm and, perhaps, faster digitization electronics. Second, while there is an associated loss in sensitivity, the magnitude of this loss can depend on the laser design (primarily the cavity finesse). As shown in the description above for at least one commercially available swept source laser, for example, this loss in sensitivity is only about 1 dB. Finally, no additional complicated signal processing or image processing techniques are required. Non-linearity in the cavity length variation can be managed using simple numerical dispersion compensation algorithms. For example and without limitation, dispersion compensation algorithms and methods can be used such as those disclosed in U.S. Pat. No. 7,719,692, which is incorporated by reference herein in its entirety.

The generation of two distinct types of image artifacts has been observed when using this method. First, faint but sharp "ghost images" in generating the fall-off plots only at the deepest end of the imaging depth was observed. However, these artifacts appeared even when the cavity length offset was zero. These artifacts can be clearly seen in FIG. 3A, as faint reflectors between about 6 mm and about 10 mm. However, these artifacts were not sufficiently bright to appear in any of the biological images. The second type of artifact was brighter but highly dispersed ghost images that only appeared at the deepest end of the imaging depth. Examples of these artifacts can be seen in FIG. 5 (bottom) and FIG. 6 (bottom), at the top of the images, as faint ghosts of the pupil (in FIG. 5—bottom) and cornea (in FIG. 6—bottom).

It appears that these artifacts can be attributed to two sources. First, non-linearity in the cavity length variation might give rise to multiple phase modulation frequencies, or even harmonics of the phase modulation frequency that are then aliased into the passband of the system electronics. These higher order modulation frequencies can create additional "ghost" images centered at different depths. Second, the k-clocks used for the 840 nm and 1040 nm sources were designed for imaging depths of about 2.9 mm and about 3.7 mm, respectively, and were not intended to be interpolated out to about 9.4 mm and about 12.4 mm. Thus, the artifacts may also be caused by inaccuracies in the wavenumber recalibration.

In practice, these artifacts only appeared at the deepest imaging depths where the sensitivity is poor, and are also so faint that for biological imaging, they may only be visible in the presence of very bright reflectors or averaged images. Nevertheless, the wavenumber recalibration issue can be easily addressed in future designs employing the same lasers by constructing a Mach-Zehnder interferometer with a longer mismatch, rather than using a lasers' internal clock. Addressing the non-linearity of the cavity length variation is a more challenging problem, and may not be necessary as the artifacts were generally unobtrusive.

It is worth noting that the phase modulation used to generate all of the experimental data in this work was generated as a by-product of the designs of the two lasers used. A laser could be deliberately designed to create a cavity length variation that would exhibit significantly better performance. An ideal laser can create a pure, linear-in-wavelength cavity length variation (and thus create fewer, if any, ghost image artifacts), can have a high finesse (ensuring that the sensitivity loss with increasing cavity length offset is minimized), and, in some embodiments, can allow for user control of the axial position shift (by adjusting the slope of the cavity length variation). Such a laser can be valuable for extended depth SSOCT imaging applications, and can simplify even further this technique for resolving the complex conjugate ambiguity in SSOCT.

Optical Delay Lines

As described above, the use of coherence revival heterodyning can have the generation of a large group delay in the reference arm, and also may introduce a group velocity dispersion and higher order dispersion. This group velocity dispersion can be balanced or compensated, either by hardware or software dispersion compensation.

Dispersive optical delay lines can be used to generate large group delays with a compact form factor and can also be used to implement hardware dispersion compensation. Hardware dispersion compensation can be particularly valuable for situations where amount of dispersion introduced by the cavity exceeds the capacity that software dispersion compensation algorithms can correct.

There are numerous potential optical designs that are capable of creating a large group delay and introducing group velocity dispersion. In general, these designs can employ a diffractive element (transmissive or reflective grating, prism, holographic material or other diffractive element) to split broadband light into its wavelength components, and then send each wavelength component through an optical path that depends on its wavelength. The individual wavelengths can then be recombined using another diffractive element. Some configurations might reuse the same diffractive elements, while other designs may direct light towards two or more diffractive elements sequentially. Regardless of whether a single or multiple diffractive elements are used, these optical systems can also be designed to be "retro-reflecting", meaning that the output of the system retraces the path of the input, or "transmissive", meaning the output port is separate from the input. Retro-reflective configurations are well-suited to be used as the reference arm of an OCT interferometer, but may also be used in conjunction with an optical circulator as an in-line modulator. Transmissive designs may be used as a transmissive reference arm or as an in-line modulator without requiring a circulator. A retro-reflective configuration, based on a single diffractive element that is quadruple passed, was used to demonstrate reduction to practice and is discussed extensively below and shown in FIG. 8A. A transmissive version of the same design can be envisioned by simply replacing the retro-reflecting mirror with a fiber coupling lens and an output optical fiber, though such a system would only create half of the phase delay of the retro-reflecting system.

Figure 9:
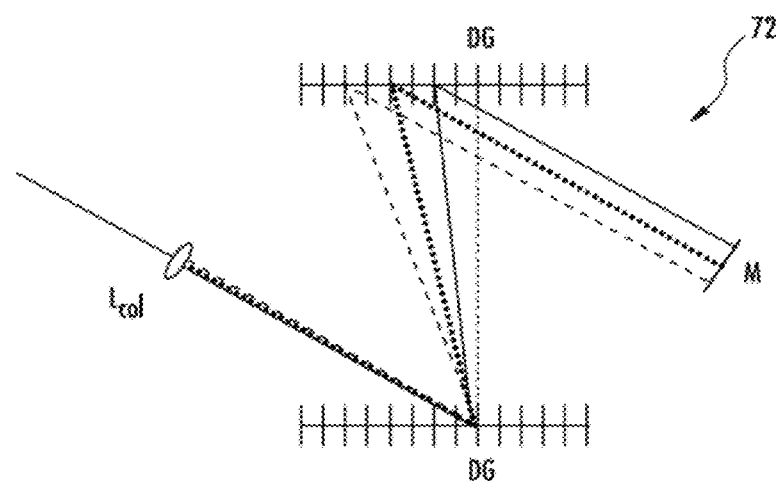
FIG. 9 illustrates a schematic view of an embodiment of a retro-reflecting dual-grating-based optical delay line according to the present subject matter herein.

An alternative design which employs two diffractive elements and a retro-reflecting mirror is shown in FIG. 9, which illustrates a schematic view of an embodiment of a retro-reflecting dual-grating-based optical delay line 72 according to the present subject matter herein. Retro-reflecting dual-grating-based optical delay line 72 comprises a collimating lens $L_{col}$, a diffraction grating DG, and a mirror M. This system can also be designed to impart a linear, wavelength dependent phase delay. A transmissive version of this design can be constructed by simply "unfolding" the system about the mirror, and can have two additional diffractive elements, a fiber coupling lens and an output fiber.

Dispersive Optical Delay Line

Figure 8A:
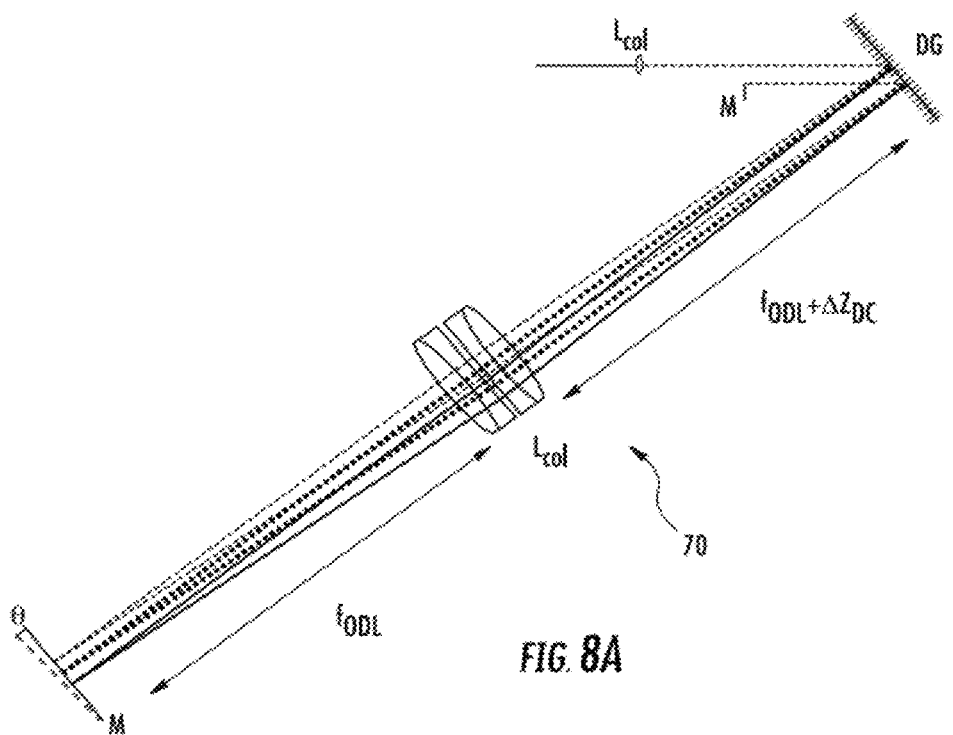
FIG. 8A illustrates a schematic view of an embodiment of a retro-reflecting grating-based optical delay line according to the present subject matter herein.

One possible implementation of this technique employs a grating-based dispersive optical delay line (DODL), which employs a single, quadruple passed diffractive element in a retro-reflecting configuration. The DODL can be similar in design to the rapid scanning optical delay lines (RSOD's) that have been used in the fastest iterations of time-domain OCT systems, but differs in that the scanning mirror in the image plane of the grating lens is replaced with a mirror at a fixed angle. When carefully designed, such a DODL can provide a large group delay while also introducing an adjustable amount of group velocity dispersion. FIG. 8A shows a schematic of one such DODL, generally designated 70. DODL 70 is a retro-reflecting grating-based optical delay line. DODL 70 comprises a collimating lens $L_{col}$, a diffraction grating DG, a compound achromatic lens $L_{ODL}$ with a focal length $f_{ODL}$, an offset for dispersion compensation $\Delta z_{DC}$, gold mirrors M, and a mirror angle θ. The different lines represent ray traces at wavelengths of 1090 nm, 1040 nm, and 990 nm respectively. A transmissive delay line can be created from the same design simply by replacing the retro reflecting mirror with a fiber coupling lens and output fiber RSOD's have been used extensively in TDOCT due to their ability to provide rapidly scanned group delays, while also providing precise control of the Doppler frequency and dispersion compensation. Design features and considerations are described in detail in the literature, so only the relevant parameters, the free-space phase and group pathlengths, will be discussed here.

The phase shift for a single pass through the DODL (double pass through the grating), as a function of wavelength, can be given by:

$$\phi(\lambda) = \frac{4\pi\theta x}{\lambda} + \frac{4\pi\theta f_{ODL}(\lambda - \lambda_0)}{p\lambda} \quad (11)$$

where θ is the mirror angle, x is the pivot offset, $f_{ODL}$ is the lens focal length and p is the grating pitch. In a relevant adaptation of this delay line for use with a coherence revival-based heterodyne SSOCT system, the mirror would be held at a fixed but adjustable angle as the wavelength is swept in time. This behavior can be modeled by defining the pivot offset, x, to be a function of wavelength. As the light propagating through the system at any instant is virtually monochromatic, the second term is always negligible and can be neglected.

As the optical delay line is designed such that the center wavelength diffracts normal to the grating, we define the pivot offset to be equal to zero for the central wavelength. Making use of the grating equation, it can be shown that the relationship between the instantaneous wavelength and the diffracted angle is given by:

$$\theta_d(\lambda) = \arcsin\left(\frac{\lambda - \lambda_0}{p}\right) \approx \frac{\lambda - \lambda_0}{p} \quad (12)$$

This equation also makes use of the small angle approximation, which introduces less than 0.02% error over the range of diffraction angles used in our experiments (−30 mrad to 30 mrad). The pivot offset, as a function of wavelength, is then given by this diffracted angle multiplied by the lens focal length:

$$x(\lambda) = f_{ODL}\frac{\lambda - \lambda_C}{p} \quad (13)$$

Thus, the phase shift as a function of wavelength becomes:

$$\phi(\lambda) = \frac{4\pi\theta f_{ODL}}{p}\left(\frac{\lambda - \lambda_0}{\lambda}\right) \quad (14)$$

As expected, this result is exactly equal to what would be obtained by simply setting the pivot offset to zero in equation (9) above. Ultimately, we are interested in the phase delay as a function of wavelength, defined as:

$$t_\phi = \frac{\phi(\omega)}{\omega} = \frac{\phi(\lambda)}{2\pi c}\lambda \quad (15)$$

Here, ω is the angular optical frequency and c is the speed of light. Applying this relationship to equation (12) yields:

$$t_\phi(\lambda) = \frac{2\theta f_{ODL}(\lambda - \lambda_0)}{pc} \quad (16)$$

Thus, the free-space phase pathlength difference, relative to the central wavelength, is given by:

$$\Delta l_\phi(\lambda) = \frac{2\theta f_{ODL}(\lambda - \lambda_0)}{p} \quad (17)$$

As expected, the free-space phase pathlength varies linearly with wavelength. To clarify, this pathlength difference is applied in a single pass through the DODL (double pass through the grating).

Ordinarily, the DODL creates a linear phase delay and also creates a constant group delay. The group delay can also be defined from the phase shift, according to the relation:

$$t_g(\omega) = \frac{\partial \phi(\omega)}{\partial \omega} \quad (18)$$

Recasting equation (11) above as a function of angular optical frequency yields:

$$\phi(\omega) = \frac{4\pi\theta f_{ODL}\left(1 - \frac{\omega}{\omega_0}\right)}{p} \quad (19)$$

Applying equation (17) to equation (18) yields:

$$t_g(\omega) = -\frac{4\pi\theta f_{ODL}}{p\omega_0} = -\frac{2\pi M}{\omega_o} \quad (20)$$

As expected, the group delay is constant with respect to optical frequency and varies linearly with the mirror angle. Thus, the group delay can be readily and rapidly adjusted by simply rotating this mirror, allowing for large group delays to be introduced in a small form factor.

The preceding derivation assumed that the DODL is aligned with the grating in the focal plane of the lens. However, as was common practice in time-domain OCT systems employing RSOD's, the delay line can also be used to introduce large amounts of group velocity dispersion by simply displacing the grating from the focal plane of the lens. Thus, the DODL can be a valuable addition to coherence revival systems, not only because it allows for the generation of large group delays, but also because it enables hardware dispersion compensation to balance the dispersion of the laser cavity.

Reduction to Practice with DODL-Based Reference Arm

An SSOCT system was constructed with two interchangeable reference arms, one in the standard configuration and one containing a DODL. Sensitivity and fall-off measurements were performed with each system and compared. Feasibility of using this technique for in vivo biological imaging was then demonstrated by imaging the anterior segments of three healthy volunteers. Design of the DODL, SSOCT system, and data processing algorithms are discussed below. Results of the system characterizations and imaging are also presented.

Reference Arms

To demonstrate convention imaging, a standard reference arm with a pathlength matched to the sample arm, was constructed. To facilitate coherence revival based heterodyne SSOCT, a DODL was also constructed, and the group delay was adjusted to be offset from the group delay of the sample arm by the laser cavity length.

Figure 8B:
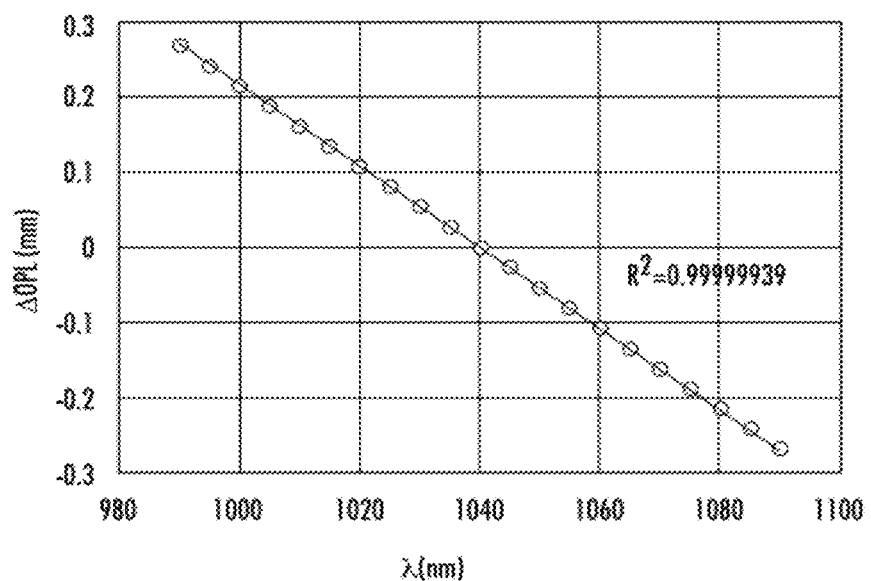
FIG. 8B is an embodiment of a plot of ray-tracing derived phase pathlength difference through the system as a function of wavelength demonstrating a linear relationship according to the present subject matter herein.

A reflective, ruled grating with 600 grooves/mm (p=1.67 µm) and a 100 mm compound achromatic lens ($f_{ODL} \approx 104.2$ mm @ 1040 nm) were used to construct the DODL. The DODL was modeled in ray tracing software (Zemax) to calculate the optical pathlength as a function of input wavelength when the grating was located in the focal plane of the lens as shown in FIG. 8A. A linear fit was applied to the optical pathlength data and fit nearly perfectly as shown in FIG. 8B.

SSOCT System

Figure 10:
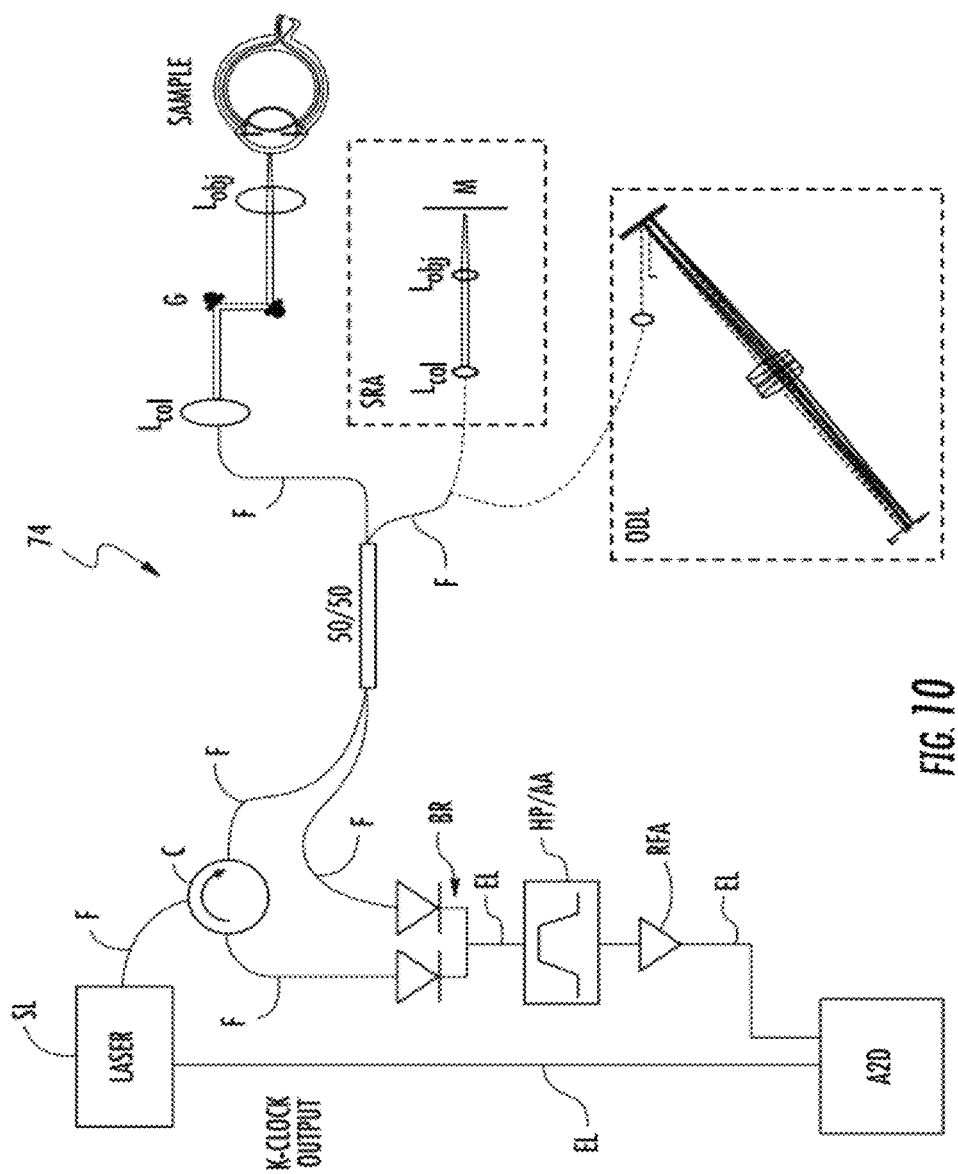
FIG. 10 illustrates a schematic view of an embodiment of a SSOCT system according to another embodiment of the presently disclosed subject matter.

An embodiment of a retro-reflecting grating-based optical delay line SSOCT system 74 is depicted in FIG. 10. SSOCT system 74 can comprise a source SL, optical fiber F, interchangeable standard reference arm SRA and optical delay line ODL, electrical connections EL, circulator C, collimating lens $L_{col}$, galvanometer scanning mirrors G, objective lenses $L_{obj}$, a mirror M, balanced receiver BR, high-pass and anti-alias filter HP/AA, RF amplifier RFA, and digitizer A2D.

The source used was a swept source laser provided by Axsun Technologies, Inc., with a central wavelength of 1040 nm, sweep bandwidth of 100 nm, repetition rate of 100 kHz, 46% duty cycle and average output power of 20 mW. Using a balanced coupler and a fiber-optic circulator produced by AC Photonics, Inc., located in Santa Clara, Calif., a balanced Michelson fiber interferometer was constructed. The sample arm had two scanning galvanometers produced by Cambridge Technology, Inc., located in Lexington, Mass., and a custom designed compound objective lens that provides sufficient depth of field to demonstrate the extended imaging depth. In compliance with the ANSI standard for ocular exposure to laser light (ANSI Z136.1), power incident on the sample arm was attenuated to 1.8 mW. Light returning from the sample and reference arms interferes in the fiber coupler and is directed to an 800 MHz balanced receiver, such as New Focus 1607 sold by Newport Corporation, located in Irvine, Calif. Output of the balanced receiver can be high-pass and anti-alias filtered, amplified and digitized in the first channel of a dual channel, 8-bit, 1 GS/s digitizer card sold such as the ATS9870 sold by Alazar Technologies, Inc. The external k-clock output of the laser is digitized on the second channel of the digitizer and used to resample the data to be linear in wavenumber.

Wavenumber Calibration and Resampling

The laser used in the system described above operates with a 46% duty cycle. This means that, even though the laser supports an A-scan rate of 100 kHz, the sweep period is actually only 4.6 µs. The internal k-clock of the laser can output a calibration signal with 1376 periods over the 4.6 µs/100 nm sweep, with a frequency that varies between approximately 250 and 350 MHz. If the spectral interferogram is sampled once per clock period, as is its intended design, this allows for a 3.7 mm maximum imaging range. However, as the signal in HSSOCT techniques is upshifted and remains Hermitian symmetric, the depth imaging range can be extended. This can be achieved in two ways. One option is to construct a k-clock with a longer pathlength mismatch and trigger the acquisition off of this longer clock. The alternative is to use the digitizer's internal clock and digitize the k-clock and to create a calibration signal. The former approach can be problematic as the pathlength mismatch required would be long enough such that the visibility of the calibration signal could be compromised. Thus, the k-clock was digitized along with the output of the balanced receiver.

Wavenumber recalibration can be carried out as follows. Both the clock and receiver signals are digitized at 1 GS/s with 8-bit resolution using custom designed LabVIEW VI owned by Duke University. The clock signal can then be upsampled and the zero-crossings of the first derivative can be recorded. The receiver data can then be resampled to be linear with respect to the intervals of these zero-crossings. It was found that the laser sweep is relatively stable, and that variation from sweep to sweep is minimal over a short period of time. Thus, for a real time image display in LabVIEW, only the clock corresponding to the first A-scan for every B-scan is processed, and signals for all other A-scans are resampled according to the calibration from this first A-scan. However, every clock signal is recorded and stored for use in post-processing for offline display. This sampling scheme supports approximately 12.4 mm of imaging depth ($z_{max}$), which extends beyond the usable depth range limited by sensitivity falloff.

Technical Notes

For SSOCT systems, 8-bit digitization can result in a marginal reduction in image quality and SNR as compared to digitization at higher bit depths. This can be in large part due to the dynamic range that is conserved by the attenuation of the source's spectral shape via balanced detection. However, imperfect balancing, which occurs as a result of technical limitations in the fabrication of balanced couplers, can result in considerable residual DC artifact. In fact, for the source and couplers used in these experiments, it has been found that this residual DC artifact can dominate over weak and moderate signals. This required the use of the higher input ranges on the digitizer, which, due to the 8-bit digitization, can result in quantization noise dominating over shot noise and limited SNR. Fortunately, because the signals of interest are shifted away from DC in hSSOCT, this residual DC artifact can be removed by high-pass filtering before digitization. After high-pass filtering, lower input ranges can once again be used, and quantization noise no longer limited SNR.

It is noted that the two fiber paths from the coupler to the balance receiver generally should be pathlength matched for this system. While this is not ordinarily a concern for SSOCT systems operating at speeds on the order of tens of kilohertz or less, at faster speeds unmatched fiber lengths in the receiver arms can result in undesirable destructive interference. This occurs when the spectral interferogram fringe wavelengths approach the fiber pathlength mismatch, such that the orthogonal components in each detection arm are no longer in phase. For the 4.6 μs sweep, a fringe signal with 1000 periods will have a wavelength of 1.32 meters, corresponding to approximately 0.9 meters of fiber. Mismatches on the order of this length can cause the fringes in the two arms of the balanced detection to move in and out of phase with each other, with the relative phase shift depending on the fringe frequency. As a result, the fringes can destructively and constructively interfere as a function of fringe frequency, resulting in an undesired signal modulation along the depth scan. This phenomenon can be avoided by ensuring that the fiber lengths in the detection arms are matched.

Using a system similar to system 74 depicted in FIG. 10, a sensitivity of 101.5 dB was measured (66.4 dB measured with a −35.1 dB calibrated reflector) with an average power of 5.0 mW incident on the sample. Neglecting coupling losses, the theoretical shot-noise limited sensitivity expected was 106.8 dB. The 5.3 dB discrepancy can be explained by coupling losses (measured to be 3.5 dB), amplification noise (0.7 dB) and excess photon noise due to imperfect balancing in the balanced detection scheme. A similar sensitivity was measured using a standard reference arm (96 dB versus a theoretical of 101 dB with 1.4 mW incident on the sample). Axial resolution, measured as the FWHM of the point-spread function from a mirror reflector, was found to be transform-limited in both cases at 6.7 microns, when using the spectrum un-windowed. Windowing the spectrum with a hamming window yielded an axial resolution of approximately 10 microns in both cases. Thus, it has been experimentally verified that the use of the DODL can result in no substantial loss of sensitivity or axial resolution.

Figure 11A:
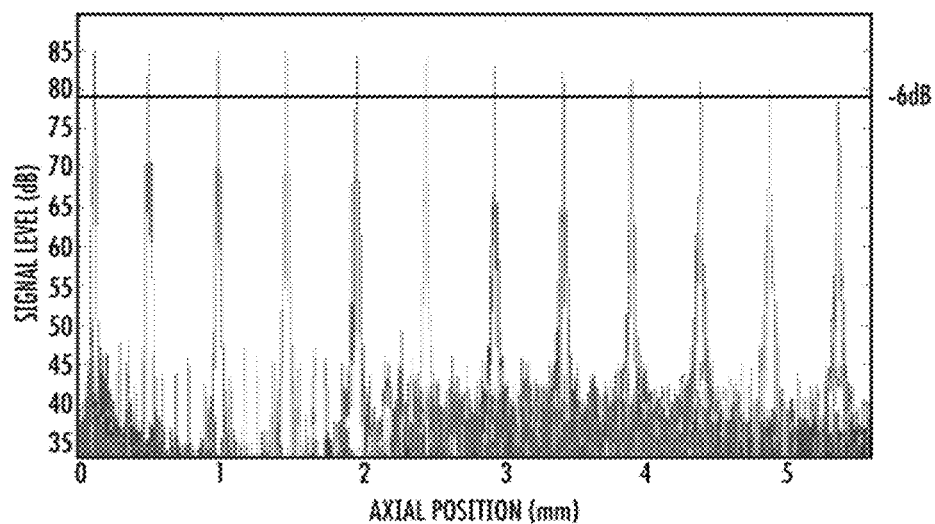
FIG. 11A is a graph of sensitivity fall-off measured using a standard reference arm, where the 6 dB imaging range is approximately 5.2 mm according to one embodiment of the presently-disclosed subject matter.
Figure 11B:
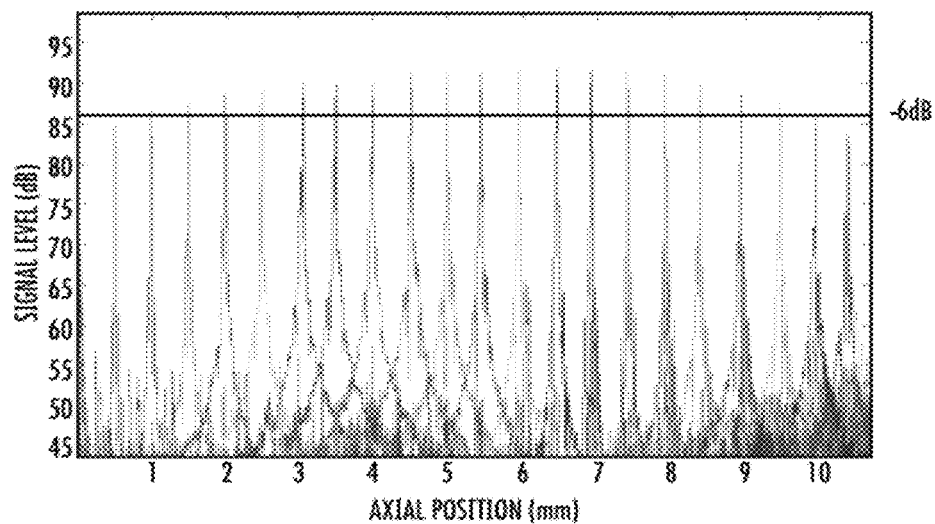
FIG. 11B is a graph of sensitivity fall-off measured using an ODL reference arm, wherein the 6 dB imaging range is approximately 9.2 mm according to one embodiment of the presently-disclosed subject matter.

Demonstration of Extended Imaging Depth and Increased Sensitivity Fall-Off Range Sensitivity fall-off was measured using both the standard reference arm (SRA) and DODL. Measurements using the SRA showed a single sided $z_{6\,dB}$ of about 5.2 mm as shown in FIG. 11A. Measurements using the DODL yield an imaging range over which the sensitivity fall-off is less than 6 dB of approximately 9.1 mm, ranging from about 0.9 mm to about 10.0 mm as shown in FIG. 11B. The limited electronic bandwidth of the digitizer accounts for the slight reduction in the imaging range of the hSSOCT system from the expected imaging range of about 10.4 mm (i.e. twice the range of the system with the SRA).

Demonstration of Feasibility for In Vivo Imaging

Figure 12:
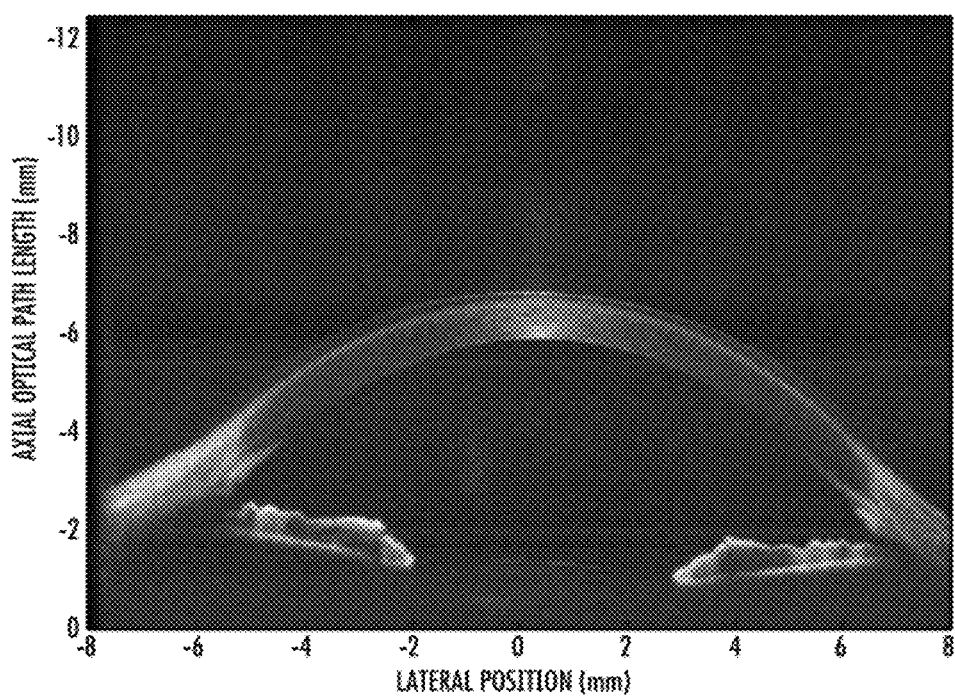
FIG. 12 is an image of an in vivo anterior segment b-scan showing a contact lens, cornea, iris, and anterior crystalline lens surface according to another embodiment of the presently-disclosed subject matter.
Figure 13:
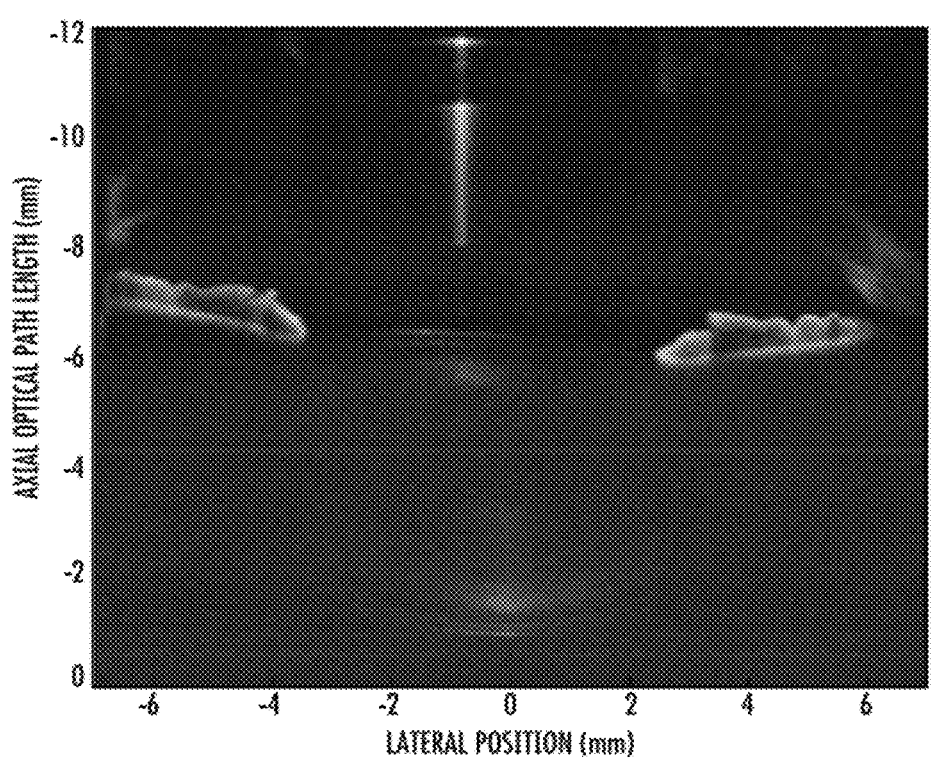
FIG. 13 is an image of an in vivo anterior segment b-scan showing a cornea, iris, and anterior and posterior crystalline lens surface according to another embodiment of the presently-disclosed subject matter.
Figure 14:
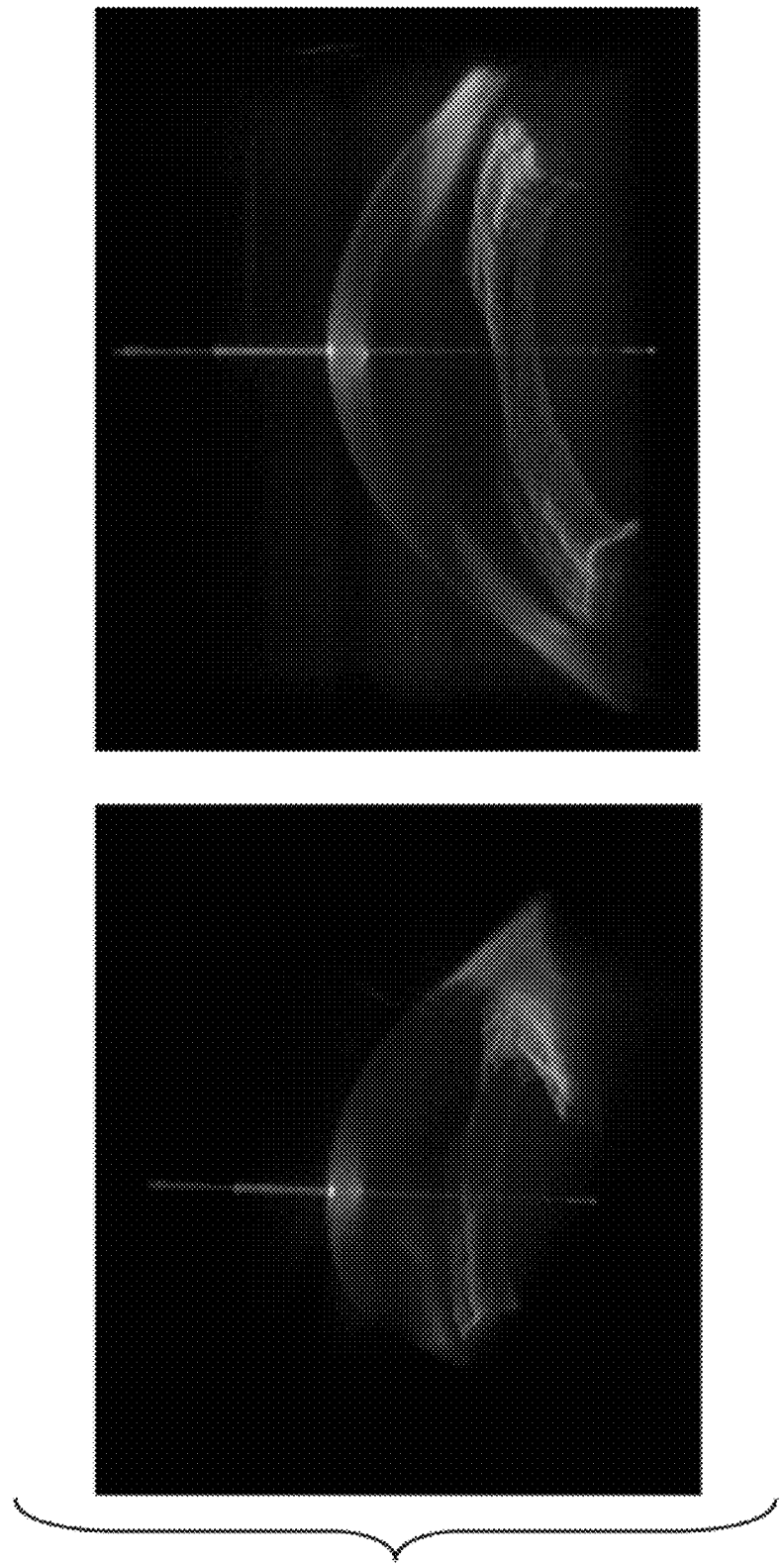
FIG. 14 is an image of an in vivo anterior segment volume showing a cornea, iris, and anterior crystalline lens surface according to one embodiment of the presently-disclosed subject matter.

To demonstrate the feasibility of this method for in vivo ophthalmic imaging, the anterior segments of three healthy volunteers were imaged. FIGS. 12 and 13 show representative anterior segment B-scans, acquired with 1000 A-scans/B-scan, registered and averaged over about 10 frames for a total acquisition time of about 100 ms. FIG. 12 shows an image of an in vivo anterior segment B-scan showing a contact lens, cornea, iris, and anterior crystalline lens surface. The image comprises about 1000 (lateral)×about 2304 (axial)×about 10 (averages) samples, acquired in about 100 ms. FIG. 13 shows an image of an in vivo anterior segment B-scan showing a cornea, iris, and anterior and posterior crystalline lens surfaces. The image comprises about 1000 (lateral)×about 2304 (axial)×about 10 (averages) samples, acquired in about 100 ms. FIG. 14 shows an image of an in vivo anterior segment volume showing cornea, iris, and anterior crystalline lens surface. FIG. 14 shows two projections of a representative anterior segment volume, acquired with 1000 A-scans/B-scan and about a 150 B-scans/volume for a total acquisition time of about 1.5 seconds per volume. For example, the image comprises about 1000 (lateral)×about 2304 (axial)×about 10 (averages) samples, acquired in about 100 ms Video recording was made demonstrating multiple projections of this volume, as well as the raw 3D data.

The image in FIG. 12 was acquired such that the volunteer's contact lens and cornea were near the focus of objective lens. As a result, the cornea appears bright and continuous. However, due to the extensive depth range of the HSSOCT system and the limited depth of focus of the objective lens, defocus results in poor visibility of the crystalline lens. The image in FIG. 13 was acquired with the objective lens focus within the crystalline lens, demonstrating simultaneous imaging of the entire anterior segment, from the anterior surface of the cornea to the posterior surface of the lens. However, again due to limited depth of focus, visibility of the curvature of the cornea is poor. This phenomenon might be addressed by designing optics with an even longer depth of focus, though this would come at the expense of lateral resolution.

Extension to SDOCT

Although the discussion above has dealt primarily with SSOCT, coherence revival techniques can also be applied to spectral domain OCT (SDOCT) systems that employ appropriate light source and/or spectrometer configurations. In SDOCT, spectral interferograms are recorded spatially on a spectrometer, as opposed to temporally on a photodiode, as in SSOCT. Nevertheless, the detection schemes are analogous.

In SSOCT, the sensitivity fall-off can be determined by the source's instantaneous linewidth, and is often characterized by the distance at which the sensitivity is reduced by 6 dB (referred to as $z_{6\,dB}$). The deepest resolvable imaging depth (referred to as $z_{max}$) can be Nyquist limited by the spectral sampling interval, which can be determined by the laser sweep speed and the sample rate. In SDOCT, the spectral resolution (defined as the spectral width of each sampling element) and spectral sampling interval of the spectrometer are analogous to the laser linewidth and spectral sampling interval in SSOCT, respectively. That is, the spectral resolution can determine the sensitivity fall-off, whereas the spectral sampling interval can limit the imaging depth. Explicitly, these relationships are given by:

$$z_{max} = \frac{\lambda_0^2}{4\delta_s\lambda} = 0.25\left(\frac{\lambda_0^2}{\delta_s\lambda}\right) \quad (21)$$

$$z_{6dB} = \frac{\ln(2)}{\pi}\frac{\lambda_0^2}{\delta_r\lambda} \approx 0.22\left(\frac{\lambda_0^2}{\delta_r\lambda}\right) \quad (22)$$

where $\lambda_0$ is the source central wavelength, $\delta_s\lambda$ is the spectral sampling interval, and $\delta_r\lambda$ is the spectral resolution. Conventional SDOCT systems employ a light source with a continuous spectrum and a spectrometer consisting of a linear detector array with near-unity fill factor. These spectrometers have a spectral resolution equal to the spectral sampling interval, and thus there is a fixed ratio between $z_{max}$ and $z_{6\,dB}$:

$$z_{-6\,dB} \approx 0.88 z_{max} \quad (23)$$

Figure 15A:
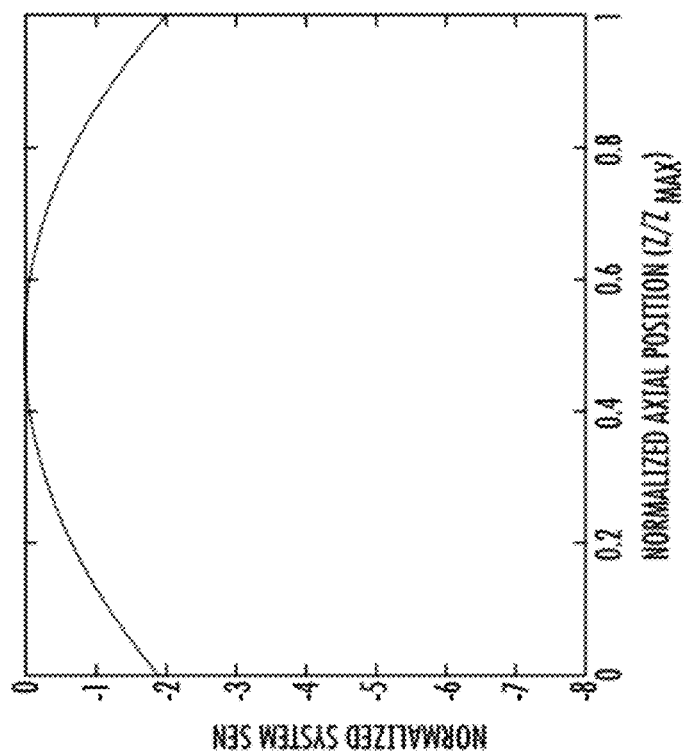
FIGS. 15A and 15B illustrate graphs of SDOCT sensitivity fall-off profiles with coherence revival heterodyning with FIG. 15A showing a conventional fall-off profile and FIG. 15B showing a fall-off profile with ideal heterodyning frequency corresponding to an axial position shift according to an embodiment of the presently-disclosed subject matter.
Figure 15B:
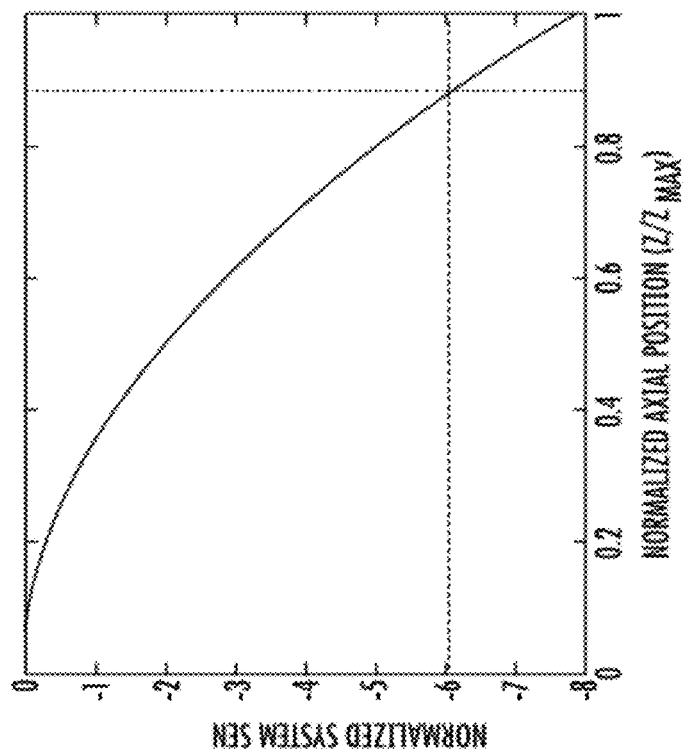

While this spectrometer design does not preclude the use of coherence revival heterodyning, it does limit the achievable improvement. Specifically, while the use of coherence revival does not extend $z_{max}$, it could serve to center the fall-off profile within the $z_{max}$ imaging range, as depicted in FIGS. 15A and 15B. In particular, FIGS. 15A and 15B illustrate graphs of SDOCT sensitivity fall-off profiles with coherence revival heterodyning. FIG. 15A shows a conventional fall-off profile, dashed lines indicate −6 dB position at z=0.88 $z_{max}$. FIG. 15B shows a fall-off profile with ideal heterodyning frequency corresponding to an axial position shift of 0.5 $z_{max}$. This embodiment could be valuable in imaging situations in which the most critical part of a sample to image is embedded within other materials, or in which it is difficult to position the sample appropriately for imaging near the edge of the SDOCT imaging range.

The benefits of coherence revival heterodyne FDOCT can also be implemented in SDOCT systems that employ light sources and/or spectrometer configurations that break the fixed ratio between the spectral resolution and spectral sampling interval. For example, this can be accomplished by using a continuous light source and a detector array within the spectrometer having less than unity fill factor, such that the spectral resolution is determined by the width of each pixel while the spectral sampling interval remains determined by the distance between them. However, such an embodiment is wasteful of source light which falls within the dead zone of the spectrometer pixels. A better approach is to utilize a light source having a comb frequency spectrum, such that one or more independent spectral lines fall upon each spectrometer pixel. With this approach, detector arrays with near unity fill factor can still be used, because the spectral resolution is determined by the line width of each comb line. This approach can be particularly well-suited to coherence revival techniques, as coherence revival itself also requires a light source with a comb frequency spectrum.

Light sources having such a comb spectrum include mode-locked lasers (e.g. femtosecond Ti-Sapphire lasers), as well as many other comb sources developed in recent decades in the optical communications industry. The remainder of the system would be analogous to the systems described above, except that an ordinary Michelson topology would be used, and a spectrometer would replace the balanced photodiodes.

Simultaneous Imaging of Multiple Imaging Depths

Figure 16:
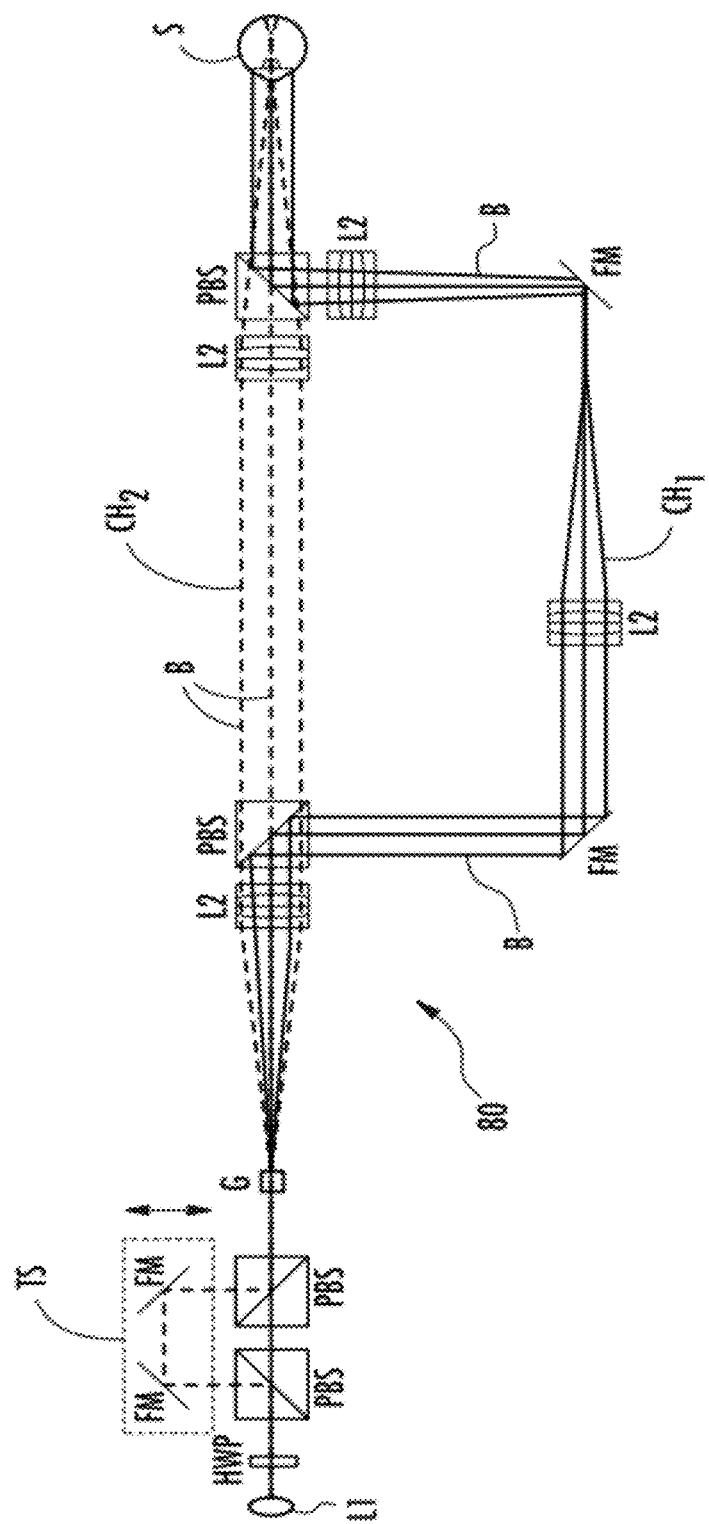
FIG. 16 illustrates a schematic view of an embodiment of a polarization encoded sample arm according to another embodiment of the presently-disclosed subject matter.

A particularly useful application of coherence revival-based FDOCT is the simultaneous imaging of multiple depths. To that end, it has been demonstrated that a coherence-revival based SSOCT system is capable of imaging both the retina and the anterior segment simultaneously. As shown in FIG. 16, the system can comprise a polarization-encoded sample arm 80 that splits the incoming light by polarization and directs orthogonally polarized beams B to the anterior segment and retina of a sample S. In particular, sample arm 80 can be configured to propagate a sample light portion of the light. Sample arm 80 can comprise at least one optical element configured to split the sample light portion in different polarizations to form multiple polarization channels $CH_1$, $CH_2$. Sample arm 80 can comprise a lens L1 where light enters and lenses L2 in channels $CH_1$, $CH_2$. Light from channels $CH_1$, $CH_2$ can be focused on at least two different locations at the same time which can be facilitated through the use of translation stage TS. For example, sample arm 80 can comprise at least one optical element, such as polarizing beam splitters PBS, that can be configured to split an initial sample light portion into polarizations to create the multiple polarization channels $CH_1$, $CH_2$ at a first location in sample arm 80 and to recombine the polarization channels $CH_1$, $CH_2$ at a second location in sample arm 80. Embodiments similar to sample arm 80 can allow for the acquisition of images of both the anterior and posterior segment of a subject's eye with no adjustment of the sample arm optics, and allows the optical design of each path to be optimized for resolution and depth-of-focus.

Path or channel $CH_2$ through sample arm 80 that can image the retina (the "retinal path") can be matched in length to a reference arm pathlength (not shown) to encode the retinal image at the baseband for conventional SSOCT imaging. The anterior segment path or channel $CH_1$ can be offset from the reference arm pathlength by a distance equal to the laser cavity length (not shown), which encoded the anterior segment interferogram with a carrier frequency. As a result, after an inverse Fourier transformation of the acquired spectral interferogram, the retinal image can appear near DC while the anterior segment image can appear shifted in depth. This phenomenon can preclude overlap of the two images while also resolving the complex conjugate artifact for the anterior segment image.

A schematic of a sample arm 80 of a multiple depth, anterior/posterior SSOCT system is shown in FIG. 16. Sample arm 80 can encoded each of the two imaging channels $CH_1$, $CH_2$ in polarization by utilizing four polarizing beamsplitter cubes PBS. Light emerging from the single mode fiber can be strongly polarized. The incoming polarization can be controlled by both the fiber polarization controller and a half-wave plate HWP before reaching a first polarizing beamsplitter cube PBS. Half-wave plate HWP can be adjusted such that the resulting polarization can be oriented at a desired angle. In some embodiments, for example, the desired angle can be between about 35 degrees-about 55 degrees to the axes of the beamsplitters. In particular, in some preferable embodiments, the desired angle can be about 45 degrees, splitting the optical power equally between the two paths. The transmitted polarization can experience a fixed delay, whereas the reflected polarization can experience a longer and variable delay that can be adjusted via a translation stage TS (dashed box in FIG. 16) that includes mirrors FM.

The two polarizations can be then recombined at a second polarizing beamsplitter cube PBS and can be scanned by galvanometer mirrors G. Reflections at galvanometer mirrors G (out of and then back into a plane parallel to the page) resulted in a rotation of the polarization, so that the P and S polarizations may be flipped. When the scanned beams reaches the third polarizing beamsplitter cube PBS, the polarization state that had initially been reflected can then be transmitted, and vice versa. Adjustment of the position of the translation stage TS can allow the relative delays between the two channels $CH_1$, $CH_2$ to be adjusted.

As the two paths are independent, scan range, resolution, and depth-of-focus trade-offs can be optimally designed for each channel $CH_1$, $CH_2$ independently. The two paths can be recombined at the fourth polarizing beamsplitter cube PBS before interfacing with the patient eye.

Notable features of the combined polarization and depth encoding schemes used in this system can be optimal optical power conservation and crosstalk rejection. The two sets of polarizing beamsplitter cubes PBS can effectively be created two polarization channels. Neglecting the finite extinction ratios of the polarizing beamsplitter cubes PBS, all of the light whose polarization is not modified in the sample can return in the appropriate polarization channel $CH_1$, $CH_2$, thereby limiting the sensitivity loss in each channel $CH_1$, $CH_2$ for dual-channel imaging to a single factor of −3 dB. Returning light, whose polarization is modified either by depolarization or birefringence in the sample, and thus contaminated the wrong polarization channel, can also be depth encoded and thus lost to imaging rather than degrading the other (anterior/posterior) image.

Figure 17:
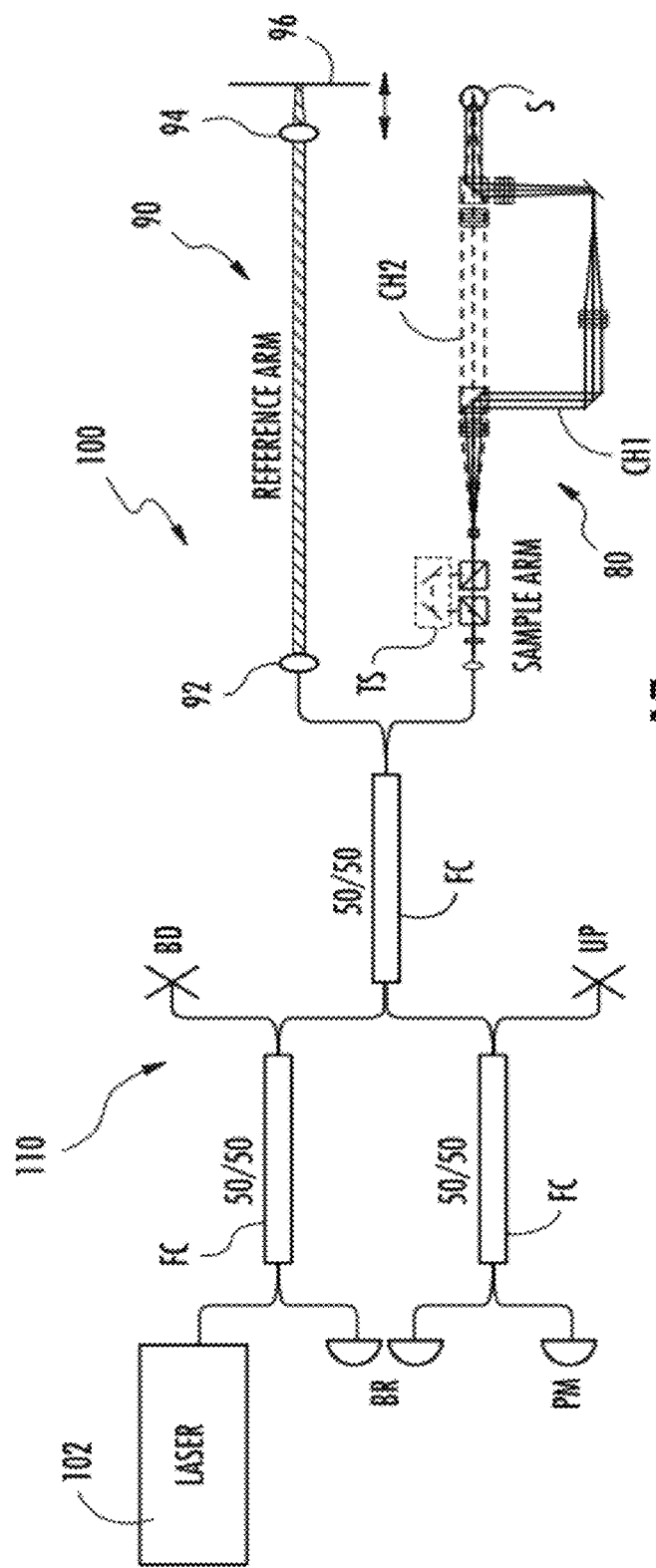
FIG. 17 illustrates a schematic view of an embodiment of a SSOCT system topology according to another embodiment of the presently-disclosed subject matter.

A schematic illustration is depicted in FIG. 17 of a multiple depth SSOCT system, generally designated 100, that uses a sample arm 80 as described above. SSOCT system 100 employs a spectrally balanced Michelson fiber interferometer 110 according to the present subject matter as described above. Interferometer 110 in SSOCT system 100 can comprise a light source 102, a balanced receiver BR, multiple beam splitting devices, such as 50/50 fiber couplers FC, arranged in an appropriate configuration, a power meter PM, a beam dump BD and unused port UP. The configuration and detailed operation of these components of Interferometer 110 will not be described in more detail here, since such a configuration is generally known in the art through the structure and operation of a conventional spectrally balanced Michelson fiber interferometer. SSOCT system 100 can also comprise a reference arm, generally designated 90, and a sample arm, generally designated 80 as described above. Reference arm 90 can comprise a collimating lens 92, a focusing lens 94, and a reference reflector 96 for reflecting a reference light portion back through the fiber couplers. As above, sample arm 80 Sample arm 80 can comprise at least one optical element configured to split the sample light portion in different polarizations to form multiple polarization channels $CH_1$, $CH_2$. Light from channels $CH_1$, $CH_2$ can be focused on at least two different locations at the same time. The dual focusing can be accomplished through the aid of translation stage TS as described above. An example of a use of a multiple depth SSOCT system as shown in FIG. 17 is described in more detail below.

In particular, SSOCT system 100, thus, can comprise light source 102 for producing a light and a resonator cavity configured to have the light travel therethrough and in which a phase modulation of the light occurs as the light travels through the resonator cavity. Reference arm 90 with a reference arm optical pathlength can be configured to propagate a reference light portion of the light. Sample arm 80 can comprise different sample arm optical pathlengths such as channels $CH_1$, $CH_2$ configured to propagate corresponding sample light portions of the light. Each sample arm optical pathlength $CH_1$, $CH_2$ can be offset from the reference arm optical pathlength by a different integer multiple of an optical pathlength of the resonator cavity. System 100 can be configured to generate an OCT interferogram corresponding to each respective sample arm optical pathlength $CH_1$, $CH_2$ of the different sample arm optical pathlengths $CH_1$, $CH_2$. System 100 can be configured to use the phase modulation of the light to separate a positive and a negative displacement of a complex conjugate component of at least one of the OCT interferograms and produce an image of at least two different depths of the sample. An example of a use of a multiple depth SSOCT system as shown in FIG. 17 is described in more detail below.

Similar to the SSOCT system topology depicted in FIG. 17, an external cavity tunable laser such as those described above operating at a 100 kHz sweep rate, output power of about 20 mW, central wavelength of about 1040 nm, and with a bandwidth of about 100 nm can be used as the source. This laser can have a conventional (single-sided) imaging range of about 5.5 mm in air (about 4.1 mm in tissue), defined as the region over which the sensitivity loss is less than about 6 dB. When used in a coherence revival configuration, the system can provide an extended imaging range of approximately 9 mm (approximately 6.8 mm in tissue). A full doubling of the 5.5 mm imaging depth was not achieved due to limited electronic bandwidth. The peak sensitivity position appeared at approximately 6 mm in depth, and the anterior segment imaging region spanned from approximately 1.5 mm to 10.5 mm. As a result, there existed a 1.5 mm region in which the retina could be imaged without limiting the imaging range of the anterior segment. This 1.5 mm retinal imaging range is comparable to the imaging depth of clinical SDOCT systems, and could be extended at the expense of anterior segment imaging range if necessary.

A balanced Michelson fiber interferometer design can be used to achieve near-ideal spectrally balanced detection. The power incident on the patient eye was 900 μW per channel. Thus, the total power incident on the patient eye was 1.8 mW, in compliance with the most stringent possible interpretation of the ANSI Z136.1 standard. Light returning from the interferometer was detected on a 1 GHz InGaAs balanced receiver (WL-BPD1GA, Wieserlabs) and digitized at 1 GS/s on an 8-bit, 500 MHz bandwidth digitizer (ATS9870, Alazar Tech).

Sample arm optics were optimized, such as by using ray tracing optical design software, to provide the optimal trade-off between resolution, aberration and depth-of-focus for each imaging depth using off-the-shelf achromatic doublets. The retinal path was designed to scan a 2.6 mm beam, pivoting through the pupil, about a 12 degree scan range (in air). This beam size was selected to provide an optimal trade-off between aberration- and diffraction-based limits to lateral resolution in a typical human eye. The anterior segment path was designed to have a lateral resolution of ~30 μm (defined as the FWHM of the PSF), and a lateral scan range of 14 mm.

Figure 18:
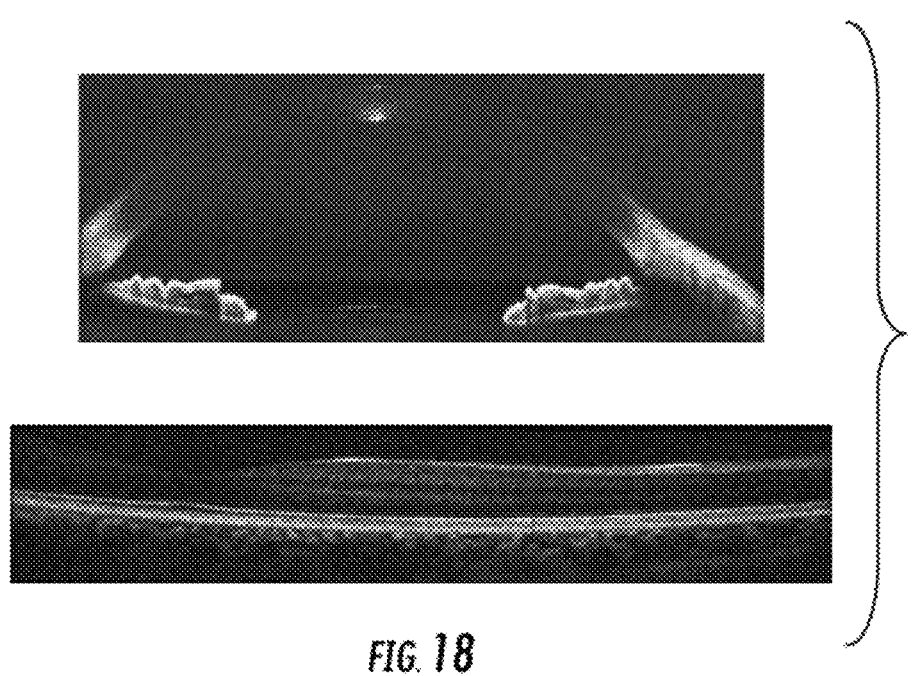
FIG. 18 illustrates example embodiments of simultaneously acquired anterior segment (top) and retinal (bottom) images according to another embodiment of the presently-disclosed subject matter.

This larger lateral resolution allowed for a much longer depth-of-field to allow imaging through the entire anterior chamber. The axial resolution for both paths was ~10 µm, limited by the spectral shaping window applied in processing. Data acquisition and processing were performed using custom designed software in LabVIEW and C. Separate dispersion compensation algorithms were applied for each depth; this is a requirement of the coherence revival technique and is described herein. The system sensitivity was measured to be ~95 dB in either arm. Sensitivity measurements were made with the HWP adjusted to direct all 1.8 mW to the arm under test. This implies that the sensitivity of each depth was 92 dB when used for simultaneous imaging. To demonstrate the feasibility of this technique for simultaneous imaging of the retina and anterior segment in vivo, imaging of healthy human volunteers was performed. Dual-depth B-scans were acquired at 100 Hz for 1000×2304 pixel images. Representative simultaneously-acquired images are shown in FIG. 18.

Benefits of this dual-depth system design include for example that it allows for the optical design in each sample path to be optimized independently, and dramatically reduces the time required for imaging of both the anterior and posterior segments. This technique could, in theory, be extended to encode as many imaging depths as would be allowed by the source's coherence revival fall-off envelope.

Systems and methods relating to OCT have thus been provided herein that can enhance imaging techniques. For example, a method for resolving complex conjugate ambiguity in OCT interferogram has been provided in which light can be produced from a light source and a phase modulation of the light can be produced within a resonator cavity through which the light travels. A reference light portion from the light source can be propagated along a reference optical pathlength. Similarly, a sample light portion from the light source can be propagated along a sample optical pathlength. The reference arm optical pathlength and the sample arm optical pathlength can be offset from each other by a multiple of an optical pathlength of the resonator cavity. The phase modulation of the light can be used to separate a positive and a negative displacement of a complex conjugate component of the OCT interferogram.

In another example, a system for resolving complex conjugate ambiguity in an optical coherence tomography (OCT) interferogram using coherence revival can be provided that comprises a light source for producing a light. The system can also comprise a resonator cavity that can be configured for the light to travel therethrough and in which a phase modulation of the light can occur as the light travels through the resonator cavity. A reference arm with a reference arm optical pathlength can be configured to propagate a reference light portion of the light source. Similarly, a sample arm with a sample arm optical pathlength can be configured to propagate a sample light portion of the light source. Within the system, the reference arm optical pathlength and the sample arm optical pathlength can be offset from each other by a multiple of an optical pathlength of the resonator cavity. The system can be configured to use the phase modulation of the light to separate a positive and a negative displacement of a complex conjugate component of the OCT interferogram. In some embodiments, the system is configured to generate the OCT interferogram based upon measurements of the reference light portion and the sample light portion.

The light can be produced in different manners in the systems and methods disclosed herein and the light can have a variety of different properties. For example, the phase modulation of the light can comprises at least one of a variance in a physical pathlength of the light, a variance in an index of refraction of the light, or a shift in a frequency of the light.

In some embodiments, the light source can comprise a laser. In some embodiments, the laser can comprise an external cavity tunable laser comprising a laser medium and the laser medium can be defined within an external resonator. In some embodiments, the resonator cavity comprises an integral and internal component of the laser. In some embodiments, a linear-in-wavelength cavity length variation can be formed with the laser. An axial position shift can be accomplished by adjusting a slope of a cavity length variation in some lasers that can be used.

The use of light sources other than a laser is also contemplated. For example, high powered diode light creating devices, such as semiconductor laser diodes that are filtered by a tunable Fabry-Perot etalon, are contemplated. The light from the light source can have a comb-like, or comb frequency spectrum. For example, a comb frequency spectrum of the light can be created within the resonator cavity.

Different configurations of the sample and reference arms used in the methods and systems are also contemplated. For example, in the some embodiments, the sample arm optical pathlength can be longer than the reference arm optical pathlength by a multiple of the optical pathlength of the resonator cavity. In some embodiments, the reference arm optical pathlength can be longer than the sample arm optical pathlength by a multiple of the optical pathlength of the resonator cavity. In these example embodiments, the multiple of an optical pathlength of the resonator cavity by which the reference arm optical pathlength and the sample arm optical pathlength are being offset from each other can comprise an integer, or a whole number. In some embodiments, a group delay can be generated in the reference arm. For example, a dispersive optical delay line (DODL) in a reference arm.

Different types of OCT systems can be used in accordance with the present subject matter. Such OCT systems can produce the OCT interferograms. For example, the OCT system can be a Fourier Domain OCT (FDOCT) system. In some embodiments, the FDOCT system can be a Spectral Domain OCT (SDOCT) system. In some embodiments, the FDOCT system can be a swept-source OCT (SSOCT) system. For example, SSOCT system can be a heterodyne SSOCT system.

In some embodiments, a numerical dispersion compensation function can be applied to the OCT interferogram. The numerical dispersion compensation can be implemented through software or hardware. For example, software can be used to apply a numerical dispersion compensation algorithm to the OCT interferogram. In some embodiments, the DODL can be useful in providing a hardware dispersion compensation to compensate for a group velocity dispersion.

In some embodiments of the present subject matter, a method for resolving complex conjugate ambiguity in an optical coherence tomography (OCT) interferogram can be provided in which light can be produced from a light source and a phase modulation of the light can be produced within a resonator cavity through which the light travels. A reference light portion from the light source can be propagated along a reference optical pathlength. Similarly, a sample light portion from the light source can be propagated along a sample optical pathlength. The reference arm optical pathlength and the sample arm optical pathlength can be offset from each other by a multiple of an optical pathlength of the resonator cavity. A positive and a negative displacement of a complex conjugate component of the OCT interferogram can then be separated. For example, coherence revival heterodyning can be used to separate a positive and a negative displacement of a complex conjugate component of the OCT interferogram.

In some embodiments of the present subject matter, an OCT interferometer system can be provided that comprises a light source having a resonator cavity for producing light. The OCT interferometer system can also comprise a reference arm with a reference arm optical pathlength and a sample arm with a sample arm optical pathlength, the reference arm optical pathlength and the sample arm optical pathlength being offset from each other by a multiple of the resonator cavity optical pathlength.

In some embodiments of the present subject matter, an OCT interferometer system can be provided that comprises a light source for producing a light and a resonator cavity configured for the light travel therethrough and in which a phase modulation of the light can occur as the light travels through the resonator cavity. The resonator cavity can have a cavity optical pathlength. The OCT interferometer system can also comprise a reference arm with a reference arm optical pathlength and a sample arm with a sample arm optical pathlength, the reference arm optical pathlength and the sample arm optical pathlength being offset from each other by a multiple of the cavity optical pathlength.

In some embodiments of the present subject matter, an optical coherence tomography (OCT) method for simultaneously imaging multiple depths of a sample can be provided that can comprise producing a light from a light source and producing a phase modulation of the light within a resonator cavity through which the light travels. A reference light portion from the light can be propagated along a reference optical pathlength. Multiple sample light portions from the light can be propagated along respective multiple sample arm optical pathlengths. Each sample arm optical pathlength can be offset from the reference arm optical pathlength by a different multiple of an optical pathlength of the resonator cavity. An OCT interferogram corresponding to each respective sample arm optical pathlength can be obtained. The phase modulation of the light can be used to separate a positive and a negative displacement of a complex conjugate component of at least one of the OCT interferograms. An image of at least two different depths of the sample can then be produced.

Similarly, an optical coherence tomography (OCT) system for simultaneously imaging multiple depths of a sample can be provided that comprises a light source for producing a light and a resonator cavity configured to have the light travel therethrough and in which a phase modulation of the light occurs as the light travels through the resonator cavity. A reference arm with a reference arm optical pathlength can be configured to propagate a reference light portion of the light. A sample arm comprising different sample arm optical pathlengths can be configured to propagate corresponding sample light portions of the light. Each sample arm optical pathlength can be offset from the reference arm optical pathlength by a different integer multiple of an optical pathlength of the resonator cavity. The system can be configured to generate an OCT interferogram corresponding to each respective sample arm optical pathlength of the different sample arm optical pathlengths. The system can also be configured to use the phase modulation of the light to separate a positive and a negative displacement of a complex conjugate component of at least one of the OCT interferograms. Additionally, the system can be configured to produce an image of at least two different depths of the sample.

In some of the embodiments, one of the multiples of the optical pathlength of the resonator cavity comprises zero (0) such that the corresponding sample arm optical pathlength is equal in length to the reference arm optical pathlength. In some embodiments, the different sample arm optical pathlengths can be formed by splitting an initial sample light portion into polarizations to form multiple polarization channels. For example, polarizing beam splitters can be configured to split an initial sample light portion into polarizations to create multiple polarization channels at a first location in the sample arm and to recombine the polarization channels at a second location in the sample arm. In some embodiments, the phase modulation of the light can be used to form the different sample arm optical pathlengths by separating an initial sample light portion into multiple channels based upon the phase modulation of the light.

In some embodiments of the present subject matter, an optical coherence tomography (OCT) method for simultaneously imaging multiple depths of a sample can be provided that can comprise producing a light from a light source. A reference light portion from the light can be propagated along a reference optical pathlength. Multiple sample light portions from the light can be propagated along respective multiple sample arm optical pathlengths. Each sample arm optical pathlength can be offset from the reference arm optical pathlength by a different multiple of an optical pathlength of the resonator cavity. An OCT interferogram corresponding to each respective sample arm optical pathlength can be obtained. An image of at least two different depths of the sample can then be produced.

In some embodiments of the present subject matter, an optical coherence tomography (OCT) interferometer system can be provided that comprises a light source for producing a light and a reference arm with a reference arm optical pathlength configured to propagate a reference light portion of the light. A sample arm can be configured to propagate a sample light portion of the light. The sample arm can comprise at least one optical element configured to split the sample light portion in different polarizations to form multiple polarization channels. Light from the channels can be focused on at least two different locations at the same time.

In some of the embodiments, each polarization channel can comprise a sample arm optical pathlength and the sample arm optical pathlengths can be variable by being configured to vary at least one of an index of refraction or a physical pathlength. In some of the embodiments, the one or more optical elements can comprise a plurality of polarizing beamsplitter cubes. For example, the plurality of polarizing beamsplitter cubes can form orthogonally polarized light beams. In some of the embodiments, the one or more optical element can comprise a plurality of polarizing prisms, such as, for example, a plurality of Wollaston prisms.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method for resolving complex conjugate ambiguity in an optical coherence tomography (OCT) interferogram, the method comprising:
   producing light from a light source;
   producing a phase modulation of the light within a resonator cavity through which the light travels, wherein the resonator cavity is disposed in the light source;
   propagating a reference light portion from the light source along a reference arm optical pathlength and a sample light portion from the light source along a sample arm optical pathlength, the reference arm optical pathlength and the sample arm optical pathlength being offset from each other by a multiple of an optical pathlength of the resonator cavity; and using the phase modulation of the light to separate a positive and a negative displacement of a complex conjugate component of the OCT interferogram produced by combining and detecting the reference light portion and the sample light portion.

2. The method according to claim 1, wherein the light source comprises a laser.

3. The method according to claim 2, wherein the resonator cavity comprises an integral and internal component of the laser.

4. The method according to claim 2, further comprising forming a linear-in-wavelength cavity length variation with the laser.

5. The method according to claim 2, further comprising controlling an axial position shift by adjusting a slope of a cavity length variation.

6. The method according to claim 1, further comprising generating a comb frequency spectrum of the light with the resonator cavity.

7. The method according to claim 1, wherein the sample arm optical pathlength is longer than the reference arm optical pathlength by a multiple of the optical pathlength of the resonator cavity.

8. The method according to claim 1, wherein the reference arm optical pathlength is longer than the sample arm optical pathlength by a multiple of the optical pathlength of the resonator cavity.

9. The method according to claim 1, wherein the phase modulation of the light comprises at least one of a variance in a physical pathlength of the light, a variance in an index of refraction of the light, or a shift in a frequency of the light.

10. The method according to claim 1, further comprising producing the OCT interferogram using a Fourier Domain OCT (FDOCT) system.

11. The method according to claim 10, wherein producing the OCT interferogram comprises producing the OCT interferogram using a Spectral Domain OCT (SDOCT) system.

12. The method according to claim 10, wherein producing the OCT interferogram comprises producing the OCT interferogram using a swept-source OCT (SSOCT) system.

13. The method according to claim 12, wherein the SSOCT system comprises a heterodyne SSOCT system.

14. The method according to claim 1, further comprising applying a numerical dispersion compensation algorithm to the OCT interferogram.

15. The method according to claim 1, further comprising generating a group delay in the reference arm.

16. The method according to claim 15, wherein generating a group delay comprises using a dispersive optical delay line (DODL) in the reference arm.

17. The method according to claim 16, further comprising applying a hardware dispersion compensation to compensate for a group velocity dispersion.

18. The method according to claim 1, wherein the multiple of an optical pathlength of the resonator cavity by which the reference arm optical pathlength and the sample arm optical pathlength are being offset from each other comprises an integer.

\* \* \* \* \*